(12) United States Patent
Ono

(10) Patent No.: US 8,970,847 B2
(45) Date of Patent: Mar. 3, 2015

(54) OPTICAL IMAGE MEASURING DEVICE

(75) Inventor: Yusuke Ono, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 7 days.

(21) Appl. No.: 13/147,536

(22) PCT Filed: Dec. 9, 2009

(86) PCT No.: PCT/JP2009/006711
§ 371 (c)(1),
(2), (4) Date: Aug. 2, 2011

(87) PCT Pub. No.: WO2010/089833
PCT Pub. Date: Aug. 12, 2010

(65) Prior Publication Data
US 2011/0286003 A1   Nov. 24, 2011

(30) Foreign Application Priority Data
Feb. 3, 2009  (JP) ................. 2009-022622

(51) Int. Cl.
*G01B 11/02* (2006.01)
*G01B 9/02* (2006.01)
*G01B 11/22* (2006.01)
(Continued)

(52) U.S. Cl.
CPC .......... *G01B 11/22* (2013.01); *A61B 3/102* (2013.01); *G01N 21/4795* (2013.01); *G01B 9/0203* (2013.01); *G01B 9/02044* (2013.01); *G01B 9/02091* (2013.01); *G01B 9/02063* (2013.01);
(Continued)

(58) Field of Classification Search
USPC ................................. 356/479, 497
See application file for complete search history.

(56) References Cited

U.S. PATENT DOCUMENTS 6,145,990 A    11/2000 Uchida
2006/0066869 A1*  3/2006 Ueno et al. .............. 356/497
(Continued)

FOREIGN PATENT DOCUMENTS

EP   1 872 713 A1   1/2008
EP     1882445 A2   1/2008
(Continued)

OTHER PUBLICATIONS

International Search Report for PCT/JP2009/006711; Mar. 16, 2010.
The Extended European Search Report; Jul. 6, 2012.
Japanese Office Action for Application No. 2009-022622 dated Jul. 25, 2013.

*Primary Examiner* — Kara E Geisel
*Assistant Examiner* — Hina F Ayub
(74) *Attorney, Agent, or Firm* — Pearne & Gordon LLP

(57) ABSTRACT

An optical image measuring device includes: an optical system that generates and detects interference light; an image forming part that forms a tomographic image based on the detection; an alignment part that performs alignment of the optical system with respect to an object; a focusing part that focuses the optical system with respect to the region of interest; a determining part that determines the suitability of the position of the optical system by the alignment part, the suitability of the focus state by the focusing part, and the suitability of the position of the tomographic image in a frame; a control part that, when it is determined that all of the positions of the optical system, position of focus state and the position in said frame are appropriate, controls the optical system and the image forming part, making it possible to obtain the tomographic image of the region of interest.

14 Claims, 17 Drawing Sheets

(51) Int. Cl.
*A61B 3/10* (2006.01)
*G01N 21/47* (2006.01)

(52) U.S. Cl.
CPC ........ *G01B 9/02068* (2013.01); *G01B 9/02089* (2013.01)
USPC .......................................... 356/497; 356/479

(56) References Cited

U.S. PATENT DOCUMENTS

| | | | |
|---|---|---|---|
| 2007/0222945 A1 | 9/2007 | Tsukada et al. | |
| 2007/0237445 A1* | 10/2007 | Hatori .............................. | 385/11 |
| 2008/0002151 A1 | 1/2008 | Hideshima et al. | |
| 2008/0100612 A1 | 5/2008 | Dastmalchi et al. | |
| 2008/0151256 A1* | 6/2008 | Kikawa et al. ................ | 356/496 |
| 2008/0151260 A1 | 6/2008 | Kikawa et al. | |
| 2009/0190092 A1 | 7/2009 | Tsukada et al. | |
| 2009/0207414 A1* | 8/2009 | Ozcan et al. ................... | 356/451 |
| 2011/0149296 A1* | 6/2011 | Tearney et al. ............... | 356/479 |

FOREIGN PATENT DOCUMENTS

| | | |
|---|---|---|
| JP | 09-276232 A | 10/1997 |
| JP | 11-325849 A | 11/1999 |
| JP | 2000-033075 A | 2/2000 |
| JP | 2002-139421 A | 5/2002 |
| JP | 2007-024677 A | 2/2007 |
| JP | 2007-252693 A | 10/2007 |
| JP | 2008-342 A | 1/2008 |
| JP | 2008-343 A | 1/2008 |
| JP | 2008-5987 A | 1/2008 |
| JP | 2006-153838 A | 6/2008 |
| JP | 2008-154725 A | 7/2008 |
| JP | 2008-154726 A | 7/2008 |
| JP | 2008-154939 A | 7/2008 |
| JP | 2008-154941 A | 7/2008 |
| JP | 2008-237237 A | 10/2008 |
| JP | 2008-289579 A | 12/2008 |

* cited by examiner

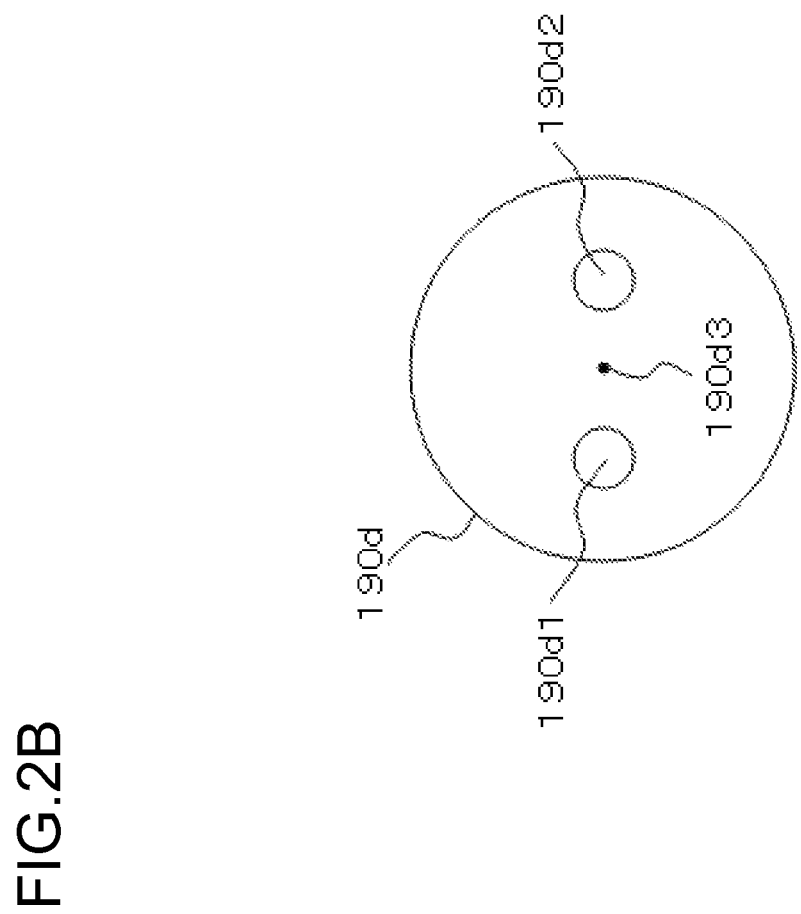

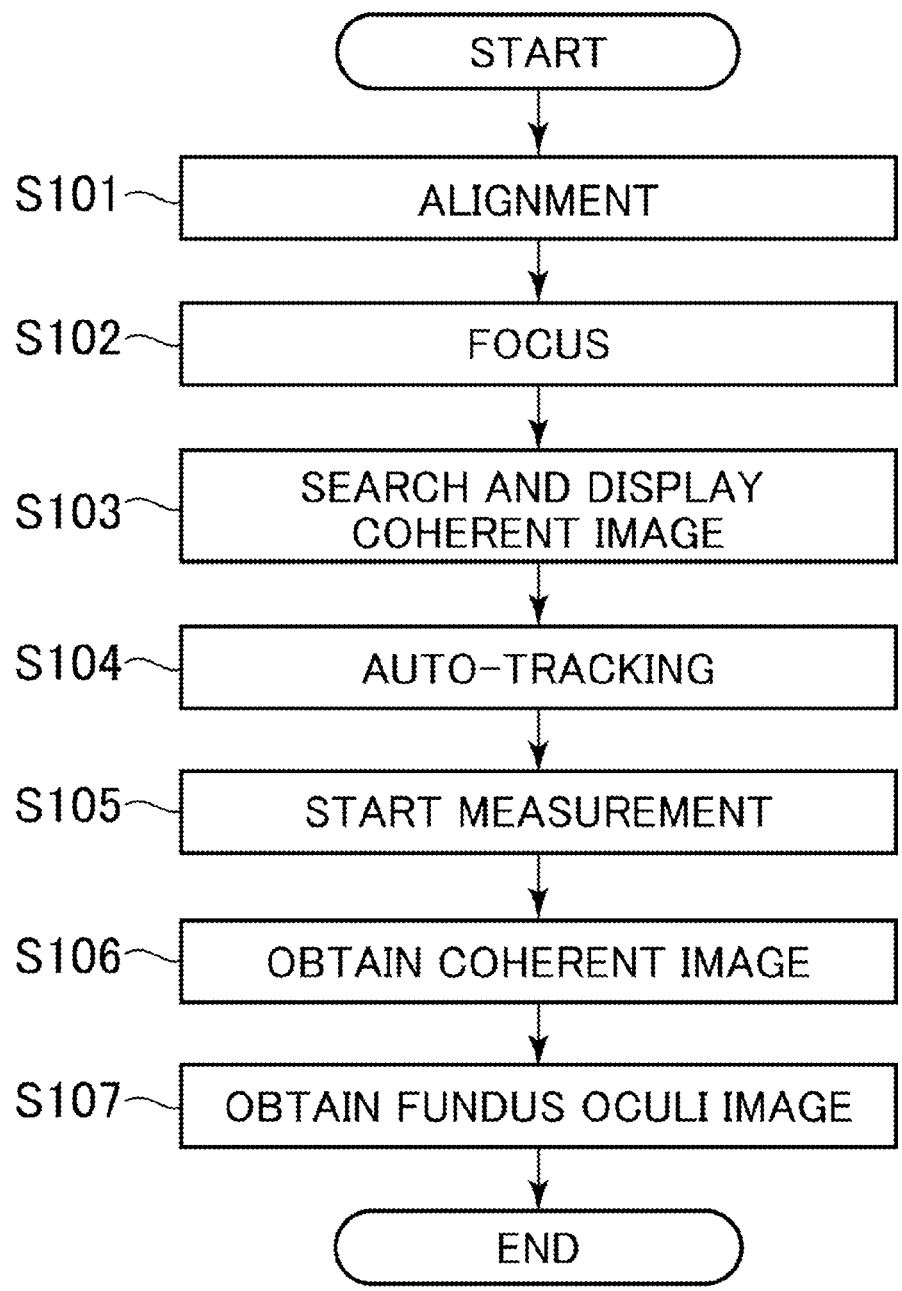

OPTICAL IMAGE MEASURING DEVICE

TECHNICAL FIELD

The present invention relates to an optical image measuring device configured to form images that show the surface morphology and internal morphology of measured objects by using a light beam.

BACKGROUND ART

In recent years, an optical image measuring technique of forming images that show the surface morphology and internal morphology of measured objects by using a light beam from a laser light source or the like has attracted attention. Unlike an X-ray CT apparatus, the optical image measuring technique is noninvasive to human bodies, and is therefore expected to be utilized more particularly in the medical field and biological field.

Japanese Unexamined Patent Application Publication No. Hei 11-325849 discloses a device to which the optical image measuring technique is applied. This device has such a configuration that: a measuring arm scans an object by a rotary deflection mirror (a Galvano mirror); a reference arm is provided with a reference mirror; and an interferometer is mounted at the outlet to analyze, by a spectrometer, the intensity of an interference light of light fluxes from the measurement arm and the reference arm. Moreover, the reference arm is configured to gradually change the light flux phase of the reference light by discontinuous values.

The device of Japanese Unexamined Patent Application Publication No. Hei 11-325849 uses a technique of so-called "Fourier Domain OCT (Optical Coherence Tomography)." That is to say, the device radiates a low-coherence light beam to a measured object, superposes the reflected light and the reference light to generate an interference light, and acquires the spectral intensity distribution of the interference light to execute Fourier transform, thereby imaging the morphology in the depth direction (the z-direction) of the measured object.

Furthermore, the device described in Japanese Unexamined Patent Application Publication No. Hei 11-325849 is provided with a Galvano mirror that scans with a light beam (a signal light), and is thereby configured to form an image of a desired measurement target region of the measured object. Because this device is configured to scan with the light beam only in one direction (the x-direction) orthogonal to the z-direction, an image formed by this device is a two-dimensional tomographic image in the depth direction (the z-direction) along the scanning direction (the x-direction) of the light beam.

Japanese Unexamined Patent Application Publication No. 2002-139421 discloses a technique of scanning with a signal light in the horizontal direction and the vertical direction to form a plurality of two-dimensional tomographic images in the horizontal direction, and acquiring and imaging three-dimensional tomographic information of a measured range based on the tomographic images. As the three-dimensional imaging, for example, a method of arranging and displaying a plurality of tomographic images in the vertical direction (referred to as stack data or the like), and a method of executing a rendering process on a plurality of tomographic images to form a three-dimensional image are considered.

Japanese Unexamined Patent Application Publication No. 2007-24677 and Japanese Unexamined Patent Application Publication No. 2006-153838 disclose other types of optical image measuring devices. Japanese Unexamined Patent Application Publication No. 2007-24677 describes an optical image measuring device that images the morphology of a measured object by scanning the measured object with light of various wavelengths, acquiring the spectral intensity distribution based on an interference light obtained by superposing the reflected lights of the light of the respective wavelengths on the reference light, and executing Fourier transform. Such an optical image measuring device is called a Swept Source type or the like.

Further, Japanese Unexamined Patent Application Publication No. 2006-153838 describes an optical image measuring device that radiates a light having a predetermined beam diameter to a measured object and analyzes the components of an interference light obtained by superposing the reflected light and the reference light, thereby forming an image of the measured object in a cross-section orthogonal to the travelling direction of the light. Such an optical image measuring device is called a full-field type, en-face type or the like.

Japanese Unexamined Patent Application Publication No. 2008-289579 discloses a configuration in which the OCT technique is applied to the ophthalmologic field. Before the optical image measuring device was applied to the ophthalmologic field, a fundus oculi observing device such as a retinal camera had been used (for example, refer to Japanese Unexamined Patent Application Publication No. Hei 9-276232).

A fundus oculi imaging device using the OCT technique has a merit that images at various depths can be selectively acquired, as compared with a retinal camera that images the fundus oculi surface. Furthermore, the fundus oculi imaging device has a merit that images with higher definition can be obtained, as compared with a retinal camera. By utilizing such OCT technique, contribution to increase of the diagnosis accuracy and early detection of a lesion are expected.

For conventional optical image measuring devices, generally, imaging is performed with the steps shown in FIG. 16. As an example, cases in which a fundus examination is performed using a device shown in Japanese Unexamined Patent Application Publication No. 2008-289579 are explained below. First, by operating a control lever, alignment of an optical system with respect to a subject's eye is performed (S101). This operation is performed, for example, by projecting bright points to the subject's eye using an alignment optical system and operating the control lever, so as to dispose the bright points that are displayed on the screen inside a bracket-shaped scale.

Next, the optical system is brought into focus with respect to the region of interest of the subject's eye (for example, the macular area, optic papilla, etc.) (S102). This operation is performed, for example, by projecting a focus target with a certain optical system and operating the focus handle. More specifically, it is performed by projecting split bright lines made of two linear bright lines as the focus target, and operating the focus handle such that the two linear bright lines are disposed on one line.

When focus is completed, search and display of a coherent image is performed (S103). This operation is to display a coherent image of a desired depth position of the fundus oculi by adjusting the optical path length of the reference light. At this time, the optical path length is adjusted so as to increase the image quality of the desired depth position. Moreover, adjustment of the optical path length may be performed manually by an operator, or it may be performed automatically by obtaining and analyzing the coherent image.

Next, by pressing a predefined button, auto-tracking is started (S104). Auto-tracking is a technology in which a light beam (signal light) is controlled to track movement of the subject's eye, so as to dispose the region of interest in nearly the middle of the coherent image. This technology is, for example, disclosed in Japanese Unexamined Patent Application Publication No. 2008-342, Japanese Unexamined Patent Application Publication No. 2008-343, Japanese Unexamined Patent Application Publication No. 2008-154725 and Japanese Unexamined Patent Application Publication No. 2008-154726.

While performing auto-tracking, at the desired timing, the operator presses the imaging switch (S105). In response to this, the device obtains a coherent image (S106), and furthermore, takes fundus oculi images (S107).

DISCLOSURE OF THE INVENTION

Problem that the Invention is to Solve

For cases in which examinations are performed with the above steps, it may be difficult to determine whether the respective state of alignment, focus, positioning of the coherent image, image quality, and auto-tracking is appropriate. In particular, for examiners not skilled in the use of the optical image measuring device, the determination thereof is difficult, and there is a high possibility of missing the measurement timing. Moreover, it is still possible that even experts with some degree of skill may miss the measurement timing.

Moreover, for conventional ophthalmic imaging systems such as retinal cameras, some systems are provided with a function for determining the state of alignment and focus and automatically performing imaging; however, it is difficult to apply these as is to the optical image measuring device. The reasons are attributed to the fact that since the image (coherent image) obtained by the optical image measuring device is higher definition than the fundus oculi image, and since the coherent image targets a narrower region than the fundus oculi image, with conventional technologies, there is a possibility that the accuracy may be insufficient. Moreover, positioning and image quality of the coherent image cannot be handled with conventional technologies.

The present invention was invented to solve the above problems, with the object of providing an optical image measuring device with which measurement can be performed easily, without missing the measurement timing.

Means for Solving the Problem

In order to achieve the aforementioned objects, a first aspect of the present invention is an optical image measuring device comprising: an optical system that splits a low-coherence light beam into signal light and reference light, generates interference light by causing said signal light propagated through a measured object and said reference light propagated through a reference object to interfere, and generates detection signals by detecting said interference light; and an image forming part that forms a tomographic image of said measured object based on said detection signals; said optical image measuring device comprising: an alignment part that performs alignment of said optical system with respect to the measured object; a focusing part that focuses said optical system with respect to the region of interest of said measured object; a determining part that determines the suitability of the position of said optical system by said alignment part, the suitability of the focus state by said focusing part, and the suitability of the position of the tomographic image of said region of interest in a frame that is formed by said image forming part; and a control part that, when it is determined that all of the position of said optical system, the position of said focus state and the position in said frame are appropriate, controls said optical system and said image forming part, making it possible to obtain the tomographic image of said region of interest.

Further, a second aspect of the present invention is the optical image measuring device according to the first aspect, wherein: said control part, when it is determined that at least one of the position of said optical system, the position of said focus state and the position in said frame is not appropriate, prohibits the acquisition of the tomographic image of said measured object.

Further, a third aspect of the present invention is the optical image measuring device according to the first aspect further comprising: a display part, wherein said control part, when it is determined that at least one of the position of said optical system, the position of said focus state and the position in said frame is not appropriate, causes said display part to display warning information.

Further, a fourth aspect of the present invention is the optical image measuring device according to the first aspect, wherein: said determining part further analyzes the tomographic image that is formed by said image forming part and determines the suitability of the image quality of said tomographic image, and said control part, when it is determined that all the position of said optical system, the position of said focus state and the position in said frame are appropriate, controls said optical system and said image forming part, making it possible to obtain the tomographic image of said region of interest.

Further, a fifth aspect of the present invention is the optical image measuring device according to the fourth aspect, wherein: said control part, when it is determined that at least one of the position of said optical system, the position of said focus state, the position in said frame and the image quality of said tomographic image is not appropriate, prohibits acquisition of the tomographic image of said measured object.

Further, a sixth aspect of the present invention is the optical image measuring device according to the fourth aspect further comprising: a display part, wherein said control part, when it is determined that at least one of the position of said optical system, the position of said focus state, the position in said frame and the image quality of said tomographic image is not appropriate, causes said display part to display warning information.

Further, a seventh aspect of the present invention is the optical image measuring device according to the fourth aspect, wherein: said optical system comprises a polarizing plate on an optical path of said reference light, wherein said control part, when it is determined that the image quality of said tomographic image is not appropriate, controls said polarizing plate such that the image quality becomes its maximum.

Further, a eighth aspect of the present invention is the optical image measuring device according to the first aspect further comprising: a tracking part that, based on the tomographic image that is formed by said image forming part, causes the irradiation position of said signal light with respect to said measured object to track movement of said measured object such that the tomographic image of said region of interest is disposed in substantially the middle inside of said frame, wherein said determining part further determines the suitability of the tracking state of the irradiation position of said signal light, and said control part, when it is determined that all of the position of said optical system, the position of said focus state, the position in said frame, and said tracking state are appropriate, controls said optical system and said image forming part, making it possible to obtain the tomographic image of said region of interest.

Further, a ninth aspect of the present invention is the optical image measuring device according to the first aspect further comprising: an imaging part that images a 2-dimensional image of said measured object on the surface that is substantially perpendicular to the traveling direction of said signal light with respect to said measured object; and a tracking part that, based on said 2-dimensional image that is imaged, causes the irradiation position of said signal light with respect to said measured object to track movement of said measured object such that the tomographic image of said region of interest is disposed in substantially the middle inside of said frame, wherein said determining part further determines the suitability of the tracking state of the irradiation position of said signal light, and said control part, when it is determined that all of the position of said optical system, the position of said focus state, the position in said frame, and said tracking state are appropriate, controls said optical system and said image forming part, making it possible to obtain the tomographic image of said region of interest.

Further, a tenth aspect of the present invention is the optical image measuring device according to either the eighth aspect or the ninth aspect, wherein: said control part, when it is determined that at least one of the position of said optical system, the position of said focus state, the position in said frame and said tracking state is not appropriate, prohibits acquisition of the tomographic image of said measured object.

Further, a eleventh aspect of the present invention is the optical image measuring device according to either the eighth aspect or the ninth aspect, further comprising: a display part, wherein said control part, when it is determined that at least one of the position of said optical system, the position of said focus state, the position inside said frame and said tracking state is not appropriate, causes said display part to display warning information.

Further, a twelfth aspect of the present invention is an optical image measuring device comprising: an optical system that splits a low-coherence light beam into signal light and reference light, generates interference light by causing said signal light propagated through a measured object and said reference light propagated through a reference object to interfere, and generates detection signals by detecting said interference light; and an image forming part that forms a tomographic image of said measured object based on said detection signals; said optical image measuring device comprising: an alignment part that performs alignment of said optical system with respect to the measured object; a focusing part that focuses said optical system with respect to the region of interest of said measured object; a tracking part that, based on the tomographic image that is formed by said image forming part, causes the irradiation position of said signal light with respect to said measured object to track movement of said measured object such that the tomographic image of said region of interest is disposed in substantially the middle inside of said frame, a determining part that determines the suitability of the position of said optical system by said alignment part, determines the suitability of the focus state by said focusing part, determines the suitability of the position of the tomographic image of said region of interest that is formed by said image forming part in a frame, determines the suitability of the image quality of said tomographic image by analyzing the tomographic image that is formed by said image forming part, and determines the suitability of the tracking state of the irradiation position of said signal light; and a control part that, when it is determined that all of the position of said optical system, the position of said focus state, the position inside said frame, the image quality of said tomographic image, and said tracking state are appropriate, controls said optical system and said image forming part, making it possible to obtain the tomographic image of said region of interest.

Further, a thirteenth aspect of the present invention is an optical image measuring device comprising: an optical system that splits a low-coherence light beam into signal light and reference light, generates interference light by causing said signal light propagated through a measured object and said reference light propagated through a reference object to interfere, and generates detection signals by detecting said interference light; an image forming part that forms part for forming a tomographic image of said measured object, based on said detection signals; and an imaging part that images a 2-dimensional image of said measured object on the surface that is substantially perpendicular to the traveling direction of said signal light, with respect to said measured object; and said optical image measuring device comprising: an alignment part that performs alignment of said optical system with respect to the measured object; a focusing part that focuses said optical system with respect to the region of interest of said measured object; a tracking part that, based on said 2-dimensional image that is imaged, causes the irradiation position of said signal light with respect to said measured object to track movement of said measured object such that the tomographic image of said region of interest is disposed in substantially the middle inside of said frame; a determining part that determines the suitability of the position of said optical system by said alignment part, determines the suitability of the focus state by said focusing part, determines the suitability of the position of the tomographic image of said region of interest that is formed by said image forming part in a frame, determines the suitability of the image quality of said tomographic image by analyzing the tomographic image that is formed by said image forming part, and determines the suitability of the tracking state of the irradiation position of said signal light; and a control part that, when it is determined that all of the position of said optical system, the position of said focus state, the position inside said frame, the image quality of said tomographic image, and said tracking state are appropriate, controls said optical system and said image forming part, making it possible to obtain the tomographic image of said region of interest.

Further, a fourteenth aspect of the present invention is the optical image measuring device according to either the first aspect, the fourth aspect, the eighth aspect, the ninth aspect, the twelfth aspect or the thirteenth aspect, wherein: said control part, when it is determined that all of the conditions are appropriate, controls said optical system and said image forming part, causing them to obtain the tomographic image of said region of interest.

Effect of the Invention

The optical image measuring device according to the present invention determines the suitability of the position of the optical system by the alignment part, the suitability of the focus state by the focusing part, and the suitability of the position of the tomographic image of the region of interest of the measured object formed by the image forming part in a frame, and when it is determined that all three of these conditions are appropriate, makes it possible to obtain the tomographic image of the region of interest.

Moreover, as another aspect of the optical image measuring device according to the present invention determines, in addition to the above three conditions, the suitability of the image quality of the tomographic image and the suitability of the tracking state of the irradiation position of the signal light, and when it is determined that all five of these conditions are appropriate, makes it possible to obtain the tomographic image of the region of interest.

According to the present invention, even for cases in which the tomographic image of measured objects having movement, such as the eyes of a living body, is to be obtained, without missing the timing at which the above various conditions are appropriate, namely without missing the measurement timing, it is possible to easily perform measurement.

BRIEF DESCRIPTION OF THE DRAWINGS

FIG. 2B is a schematic view showing an example of a configuration of an alignment optical system of the embodiment of the optical image measuring device according to the present invention.

FIG. 16 is a flow chart showing an example of an operation of a conventional optical image measuring device.

BEST MODE FOR CARRYING OUT THE INVENTION

An example of an embodiment of an optical image measuring device according to the present invention will be described in detail with reference to the drawings. In this embodiment, a device that is used in the ophthalmologic field to acquire an OCT image of a living eye will be described. A living eye is moving at all times due to eye movement such as involuntary eye movement, heartbeats, and so on. A like effect can be obtained by a like configuration also at the time of acquisition of an OCT image of a measured object other than a living eye.

In this embodiment, a configuration to which a Fourier-Domain-type method is applied will be described in detail. To be specific, in this embodiment, an optical image measuring device provided with almost the same configuration as the device disclosed in Patent Document 5 will be picked up. In a case that another configuration is applied, application of a similar configuration to that of this embodiment makes it possible to obtain similar actions and effects. For example, it is possible to apply the configuration according to this embodiment to any type of OCT device that scans with a signal light and executes measurement as in the Swept Source type. Besides, it is also possible to apply the configuration according to this embodiment to an OCT technique, such as the full-field type, in which a transverse scan with a signal light is not executed.

[Configuration]

Figure 1:
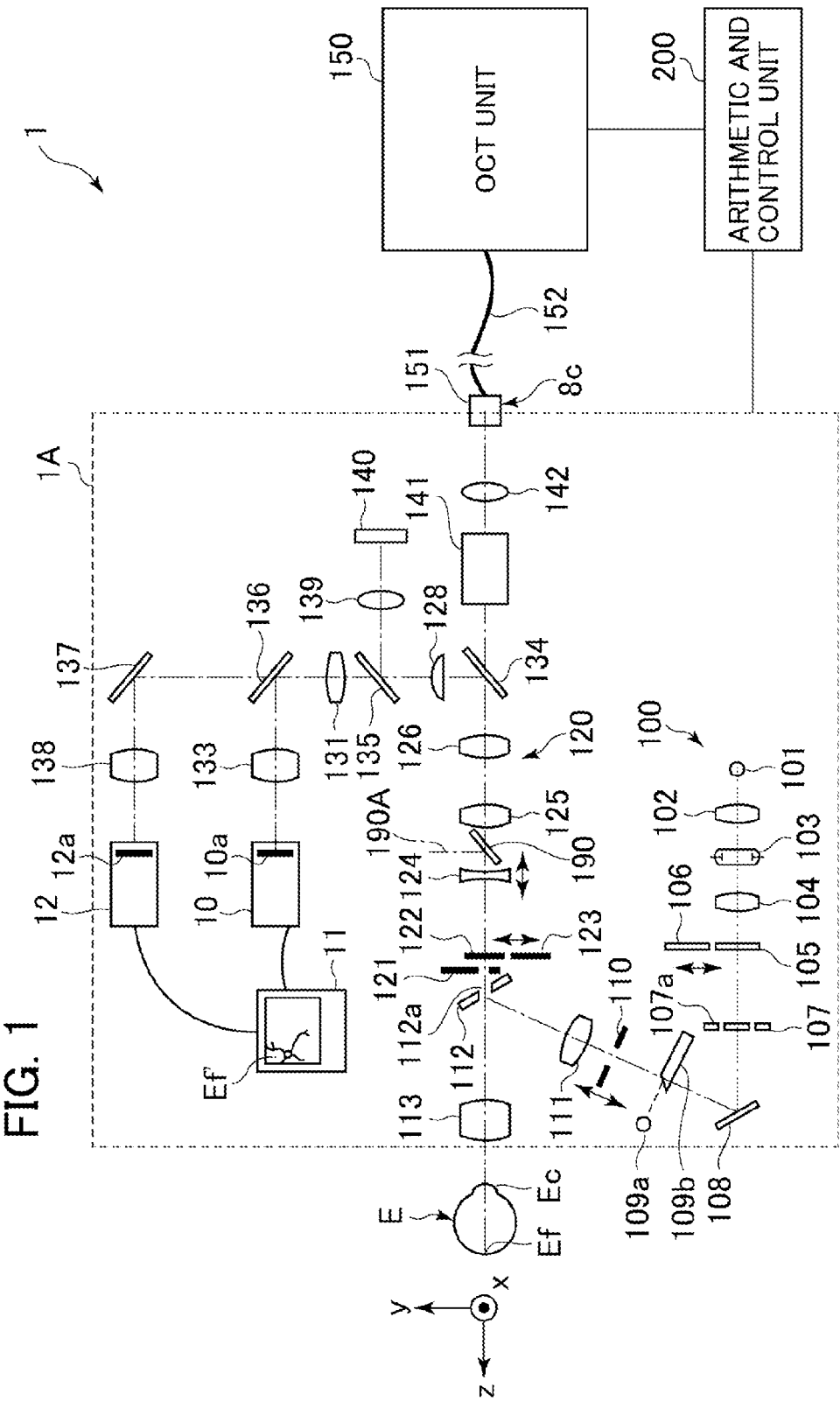
FIG. 1 is a schematic view showing an example of an entire configuration of an embodiment of an optical image measuring device according to the present invention.

An optical image measuring device 1, as shown in FIG. 1, includes a retinal camera unit 1A, an OCT unit 150, and an arithmetic and control unit 200. These components are arranged separately in several cases, or arranged together in a case. The retinal camera unit 1A has almost the same optical system as a conventional retinal camera. A retinal camera is a device that photographs the fundus oculi. Moreover, a retinal camera is utilized for photographing the morphology of fundus oculi blood vessels. The OCT unit 150 houses an optical system for acquiring an OCT image of an eye. The arithmetic and control unit 200 is provided with a computer that executes various arithmetic processes, control processes, and so on.

To the OCT unit 150, one end of a connection line 152 is attached. To the other end of the connection line 152, a connector part 151 that connects the connection line 152 to the retinal camera unit 1A is attached. An optical fiber 152a runs through inside the connection line 152 (refer to FIG. 4). The OCT unit 150 and the retinal camera unit 1A are optically connected via the connection line 152. The arithmetic and control unit 200 is connected to both the retinal camera unit 1A and the OCT unit 150 via a communication line that transmits electric signals.

[Retinal Camera Unit]

The retinal camera unit 1A has an optical system for forming a two-dimensional image showing the morphology of the fundus oculi surface. A two-dimensional image of the fundus oculi surface includes a color image and a monochrome image obtained by photographing the fundus oculi surface and a fluorescent image (a fluorescein angiography image, an indocyanine green fluorescent image, and so on).

The retinal camera unit 1A, as is the case with conventional retinal cameras, is provided with various user interfaces. Examples of the user interfaces include an operation panel, a control lever (joystick), an imaging switch, a focus handle, a display, etc. The operation panel is provided with various switches and buttons. The control lever is operated in order to three-dimensionally move a stand to which the operation panel is provided or a device body into which the optical system is built, with respect to the device base. More specifically, the control lever is used during manually performed alignment operations. The imaging switch is provided on the upper edge of the control lever, and is used in order to provide instructions on the acquisition of the fundus oculi image or an OCT image. Moreover, the imaging switch is also used while other functions are performed. The operation panel and the control lever are provided at the position of the examiner side (the rear surface) of the retinal camera unit 1A. The focus handle, for example, is provided on the side surface of the device body, and is used in order to adjust the focus (focusing). Moreover, when the focus handle is operated, a focusing lens, which is described below, is moved and the focus state is changed. The display is provided at the position of the examiner side of the retinal camera unit 1A, and displays a variety of information including the image obtained with the optical image measuring device 1, patient information, and imaging conditions. A chin rest and the forehead placement for retaining the face of the subject are provided at the position of the subject side (the front surface) of the retinal camera unit 1A.

Like a conventional retinal camera, the retinal camera unit 1A is provided with an illumination optical system 100 and an imaging optical system 120. The illumination optical system 100 radiates an illumination light to a fundus oculi Ef. The imaging optical system 120 leads a fundus oculi reflected light of the illumination light to imaging devices 10 and 12. Moreover, the imaging optical system 120 leads a signal light coming from the OCT unit 150 to an eye E, and also leads the signal light propagated through the eye E to the OCT unit 150.

As in a conventional retinal camera, the illumination optical system 100 includes an observation light source 101, a condenser lens 102, an imaging light source 103, a condenser lens 104, exciter filters 105 and 106, a ring transparent plate 107, a mirror 108, a reflection rod 109b, an illumination diaphragm 110, a relay lens 111, an aperture mirror 112, and an objective lens 113.

The observation light source 101 outputs an illumination light including a wavelength of a near-infrared in the range from about 700 to 800 nm, for example. This near-infrared light is set so as to have a shorter wavelength than a light used in the OCT unit 150 (described below). The imaging light source 103 outputs an illumination light including a wavelength of visible region a region in the range from about 400 to 700 nm, for example.

The illumination light outputted from the observation light source 101 reaches the aperture mirror 112 via the condenser lenses 102 and 104, (the exciter filters 105 and 106,) the ring transparent plate 107 (ring slit 107a), the mirror 108, the reflection rod 109b, the illumination diaphragm 110, and the relay lens 111. Besides, this illumination light is reflected by the aperture mirror 112 to enter the eye E via the objective lens 113 and illuminate the fundus oculi Ef. On the other hand, the illumination light outputted from the imaging light source 103, similarly, enters the eye E via a path from the condenser lens 104 to the objective lens 113, and illuminates the fundus oculi Ef.

The imaging optical system 120 includes the objective lens 113, (an aperture 112a of) the aperture mirror 112, an imaging diaphragm 121, barrier filters 122 and 123, a focusing lens 124, a relay lens 125, an imaging lens 126, a dichroic mirror 134, a field lens 128, a half mirror 135, a relay lens 131, a dichroic mirror 136, an imaging lens 133, the imaging device 10, a reflection mirror 137, an imaging lens 138, the imaging device 12, a lens 139, and an LCD 140. The imaging optical system 120 has almost the same configuration as in a conventional retinal camera. The focusing lens 124 is capable of moving in optical axis direction of the imaging optical system 120.

The dichroic mirror 134 reflects the fundus oculi reflected light (having a wavelength included in the range from about 400 to 800 nm) of the illumination light coming from the illumination optical system 100. Moreover, the dichroic mirror 134 transmits a signal light LS (having a wavelength included in the range from about 800 to 900 nm, for example; refer to FIG. 3) coming from the OCT unit 150.

The dichroic mirror 136 reflects the fundus oculi reflected light of the illumination light coming from the observation light source 101. Moreover, the dichroic mirror 136 transmits the fundus oculi reflected light of the illumination light coming from the imaging light source 103.

The LCD 140 displays a fixation target (an internal fixation target) for fixating the eye E. The light from the LCD 140 is focused by the lens 139, reflected by the half mirror 135, propagated through the field lens 128, and reflected by the dichroic mirror 134. Furthermore, this light is propagated through the imaging lens 126, the relay lens 125, the focusing lens 124, the (aperture 112a of the) aperture mirror 112, the objective lens 113 and so on, and enters the eye E. Consequently, the internal fixation target is projected to the fundus oculi Ef.

By changing a display position of the internal fixation target by the LCD 140, it is possible to change a fixation direction of the eye E. The fixation direction of the eye E is a fixation direction for acquiring an image centered on the macula of the fundus oculi Ef, a fixation direction for acquiring an image centered on the optic papilla, a fixation direction for acquiring an image centered on the fundus oculi center between the macula and the optic papilla, and so on, as in conventional retinal cameras, for example. The operation panel, for example, is used to change fixation directions.

The imaging device 10 includes an image pick-up element 10a. The imaging device 10 is specifically capable of detecting a light of a wavelength in the near-infrared region. In other words, the imaging device 10 functions as an infrared TV camera that detects a near-infrared light. The imaging device 10 detects a near-infrared light and outputs video signals. The image pick-up element 10a is any kind of image pick-up element (area sensor) such as a CCD (Charge Coupled Device) or a CMOS (Complementary Metal Oxide Semiconductor), for example.

The imaging device 12 includes an image pick-up element 12a. The imaging device 12 is specifically capable of detecting a light of a wavelength in the visible region. In other words, the imaging device 12 functions as a TV camera that detects a visible light. The imaging device 12 detects a visible light and outputs video signals. Like the image pick-up element 10a, the image pick-up element 12a is composed of any kind of image pick-up element (area sensor).

A touch panel monitor 11 displays a fundus oculi image Ef based on the video signals from the respective image pick-up elements 10a and 12a. Moreover, the video signals are transmitted to the arithmetic and control unit 200. The touch panel monitor 11 is an example of the above-mentioned display The retinal camera unit 1A is provided with a scan unit 141 and a lens 142. The scan unit 141 scans a target position on the fundus oculi Ef with the signal light LS outputted from the OCT unit 150.

The scan unit 141 scans with the signal light LS on the xy-plane shown in FIG. 1. For this purpose, the scan unit 141 is provided with, for example, a Galvano mirror for scanning in the x-direction and a Galvano mirror for scanning in the y-direction.

A focus optical system is comprised of the reflection rod 109b of the illumination optical system 100, along with a LED 109a. The focus optical system, as is the case with conventional retinal cameras, projects the target (split bright lines) used for focus adjustment to a subject's eye E. The reflection rod 109b is constituted such that it can be inserted or taken out with respect to the optical axis of the illumination optical system 100. One end of the reflection rod 109b has the reflection surface that is inclined with respect to the optical axis of the illumination optical system 100. Light that is output from the LED 109a is reflected onto the reflection surface, and is projected to the subject's eye E through the same path as the illumination light.

The focus optical system, in conjunction with movement of the focusing lens 124, is moved in the direction of the optical axis of the illumination optical system 100 such that the reflection surface of the reflection rod 109b and the fundus oculi Ef are optically conjugate. For cases in which the reflection surface and the fundus oculi Ef are not conjugated, the pair of split bright lines are not disposed along a straight line, but appear to be split in the lateral direction. On the other hand, for cases in which the reflection surface and the fundus oculi Ef are conjugated, the pair of split bright lines are disposed along a straight line. By referring this, focus adjustment can be performed. Focus adjustment using this type of split bright lines is widely utilized in conventional retinal cameras, etc.

On an optical path between the focusing lens 124 and the relay lens 125, a half mirror 190 is formed at a slant. The half mirror 190 acts to compose an optical path of an alignment optical system 190A shown in FIG. 2A and an optical path of the imaging optical system 120 (an imaging optical path). The alignment optical system 190A is an optical system for projecting, to the eye E, an alignment bright point used for position matching (alignment) of the optical system with respect to the eye E.

This alignment bright point is used for both an alignment to make an apex position of a cornea Ec of the eye E (a corneal apex) match the optical axes of the optical systems 100 and 120 (an alignment in the xy-direction shown in FIG. 1) and an alignment of a distance between the eye E and the optical systems 100 and 120 (the z-direction in FIG. 1; a working distance; a distance between the corneal apex of the eye E and the objective lens 113) (for example, refer to Japanese Unexamined Patent Application Publication No. 11-4808).

Figure 2A:
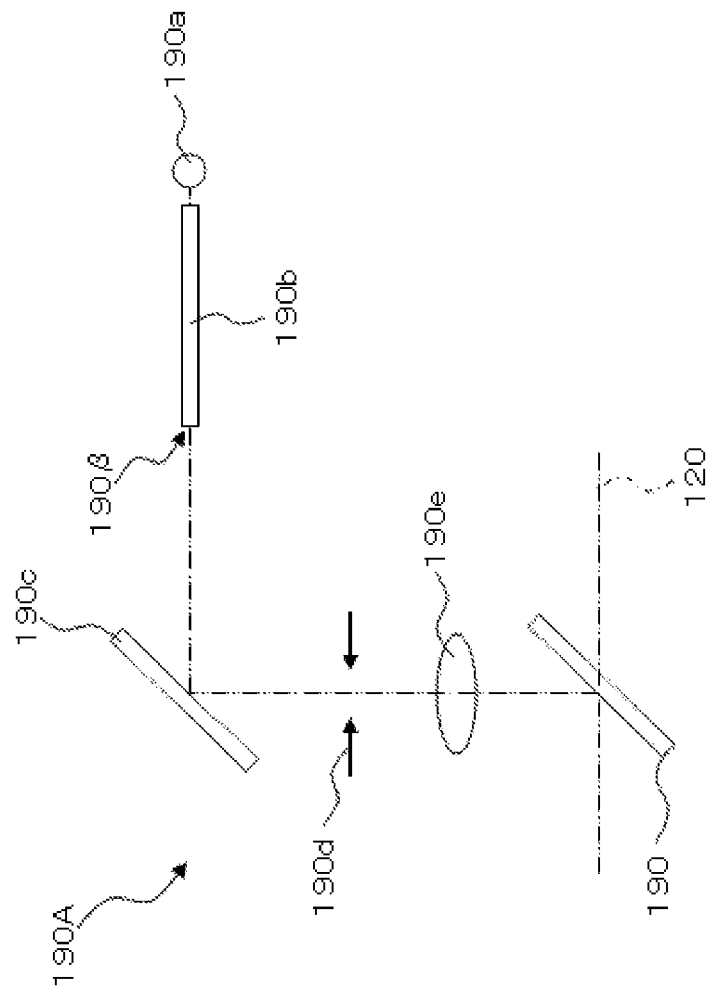
FIG. 2A is a schematic view showing an example of a configuration of an alignment optical system of the embodiment of the optical image measuring device according to the present invention.

The alignment optical system 190A, as shown in FIG. 2A, includes the half mirror 190, an alignment light source 190a, a light guide 190b, a reflection mirror 190c, a two-hole aperture 190d, and a relay lens 190e. The alignment light source 190a, for example, includes a light source such as an LED that outputs a light of near-infrared region (an alignment light).

The two-hole aperture 190d has two holes 190d1 and 190d2 as shown in FIG. 2B. The holes 190d1 and 190d2 are formed in symmetrical positions with respect to a center position 190d3 of the disk-like two-hole aperture 190d, for example. The two-hole aperture 190d is mounted so that the center position 190d3 is located on the optical path of the alignment optical system 190A.

The alignment light emitted from an emission end 190β of the light guide 190b is reflected by the reflection mirror 190c and led to the two-hole aperture 190d. The alignment light (or part thereof) having passed through the holes 190d1 and 190d2 of the two-hole aperture 190d is propagated through the relay lens 190e, reflected by the half mirror 190, and led to the aperture mirror 112. At this moment, the relay lens 190e performs intermediate imaging of an image of the emission end 190β of the light guide 190b in the center position of the aperture 112a of the aperture mirror 112 (a position on the optical axis of the imaging optical system 120). The alignment light having passed through the aperture 112a of the aperture mirror 112 is projected to the cornea Ec of the eye E via the objective lens 113.

Here, in a case that a positional relation between the eye E and the retinal camera unit 1A (the objective lens 113) is proper, that is, in a case that a distance between the eye E and the retinal camera unit 1A (a working distance) is proper and the optical axis of the optical system of the retinal camera unit 1A (substantially) matches the axis of the eye E (position of the corneal apex), two light fluxes (alignment light fluxes) formed by the two-hole aperture 190d are projected to the eye E so as to respectively form images at intermediate positions between the corneal apex and the corneal curvature center.

The cornea reflected lights of the two alignment light fluxes (the alignment light) are received by the image pick-up element 10a via the imaging optical system 120. Images captured by the image pick-up elements 10a are displayed on a display device such as a display (described later) of the touch panel monitor 11 or the arithmetic and control unit 200.

Figure 4:
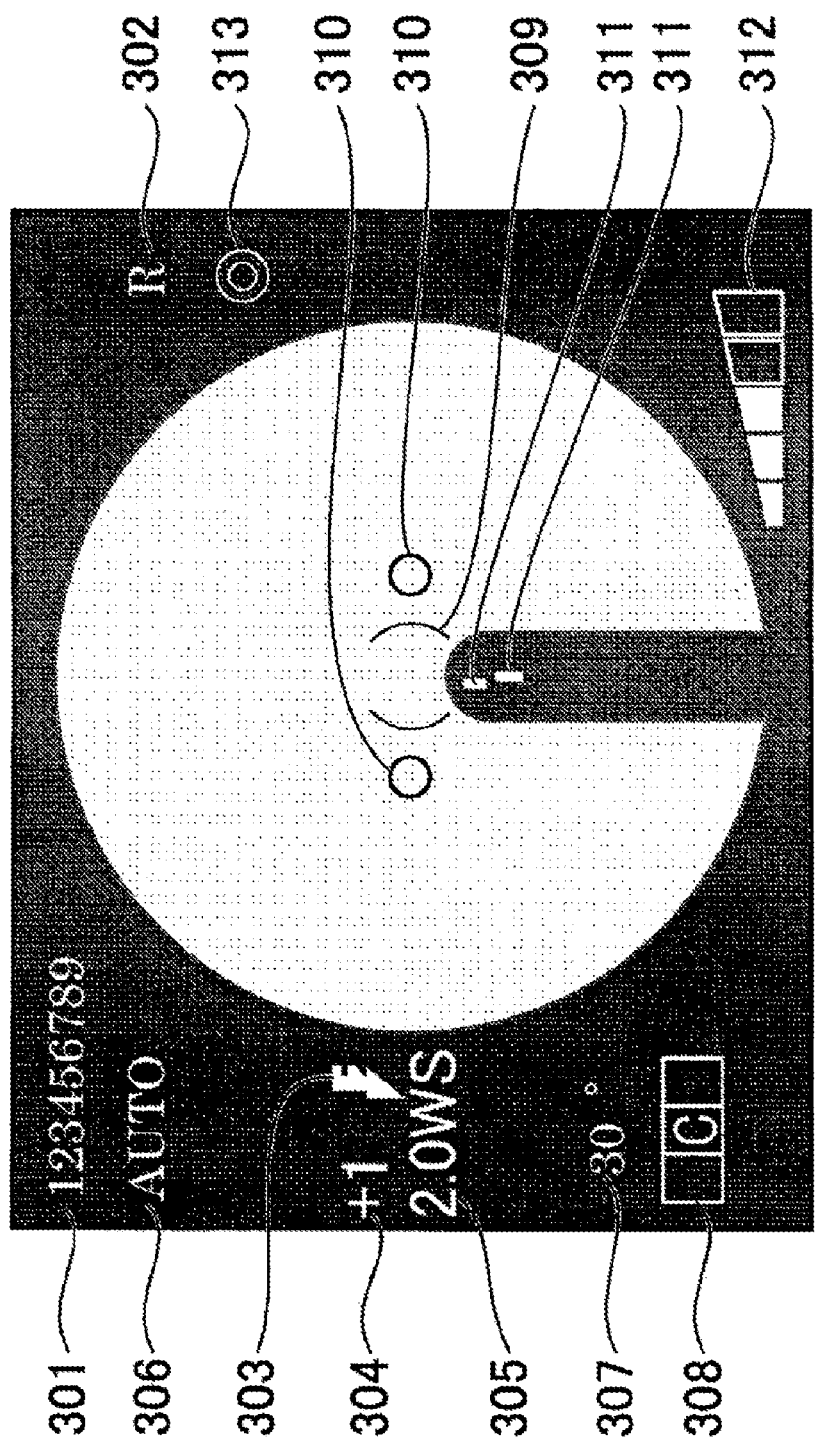
FIG. 4 is a schematic view showing an example of a configuration of a display screen in the embodiment of the optical image measuring device according to the present invention.

Here, focus adjustment and alignment adjustment are explained with reference to FIG. 4. This display screen is displayed on, for example, the touch panel monitor 11. The information displayed on this display screen includes a patient ID 301, right and left eye information 302, imaging light source charging information 303, imaging light source correction information 304, imaging light intensity level information 305, automatic imaging information 306, angle information 307, fixation position information 308, an alignment scale 309, a pair of alignment bright points 310, a pair of split bright lines 311, observation light intensity level information 312, and small pupil information 313.

The right and left eye information 302 is that showing whether the subject's eye E is the left eye (L) or the right eye (R). The imaging light source charging information 303 is that showing the charging state of the imaging light source 103 (such as a xenon lamp). The imaging light intensity correction information 304 is that indicating the correction value of the imaging light intensity that is set on the operation panel. The imaging light intensity level information 305 is that showing the setting value of the imaging light intensity. The automatic imaging information 306 is indicated for cases in which functions that automate the imaging operations such as auto-shoot (automatic shooting) or auto-focus are turned on. The angle information 307 is that showing the setting value of imaging angle of view (or magnification). The fixation position information 308 is that showing the setting value of the fixation position (or fixation direction) of the subject's eye E. The observation light intensity level information 312 is that showing the setting value of the observation light intensity. The small pupil information 313 is indicated for cases in which a small pupil aperture (not shown in the figures), which is used for cases in which the subject's eye E is the small pupil, is applied.

Here, the alignment is explained. The pair of alignment bright points 310 are light reception images of the light that is projected from the alignment optical system 190A to the subject's eye E. The alignment scale 309 is a bracket shaped image that shows the position, which is the target of the pair of alignment bright points 310. The examiner performs alignment of the optical system with respect to the subject's eye E, by operating the control lever and 3-dimensionally moving the retinal camera unit 1A such that the pair of alignment bright points 310 are placed inside the alignment scale 309.

Instead of manually performing alignment adjustment in this way, it is also possible to apply an auto-alignment function. Auto-alignment, for example, is performed by specifying the position of each alignment bright point 310 on the display screen, calculating the position deviation between each specified position and the alignment scale 309, and moving the retinal camera unit 1A such that this deviation is cancelled out. Each alignment bright point 310 is specified, for example, by calculating the luminance distribution of each alignment bright point and calculating the position of their centers of gravity based on this luminance distribution. Since the position of the alignment scale 309 is constant, for example, by calculating the displacement with the center position of the alignment scale 309 and the abovementioned position of the centers of gravity, it is possible to calculate the abovementioned deviation. It is possible to determine the moving direction and the moving distance of the retinal camera unit 1A, by referring to the unit moving distance for each of the x direction, y direction, and z direction that are previously set, namely, (for example, the previous measurement results of the moving direction and the moving distance of the alignment bright points 310 corresponding to movement of the retinal camera unit 1A in a certain direction with a certain distance). Moreover, an actuator (pulse motor, etc.) for moving the retinal camera unit 1A is provided for cases in which auto-alignment is performed.

Here, focus adjustment is explained. The pair of split bright lines 311 are presented side-by-side in the vertical direction. The examiner, in order to perform focus adjustment, by operating the focus handle, moves the focusing lens 124 and the focus optical system. Accordingly, the vertical split bright lines 311 move in the lateral direction. The examiner executes focusing by operating the focus handle, such that the vertical split bright lines 311 are positioned in a vertical straight line.

Instead of manually performing the focus adjustment in this way, it is also possible to apply an auto-focus function. Auto-focus, for example, is performed by specifying the display position of each split bright line 311 and calculating the moving direction and the moving distance of the focusing lens 124, etc., such that the vertical split bright lines 311 are positioned in a straight line. It is possible to obtain the display position of each split bright line 311, for example, by calculating the position of the center of gravity from the luminance distribution of each split bright line 311. It is possible to determine the moving direction and the moving distance, for example, by referring to the unit moving distance that was previously set (for example, the previous measurement results of the moving direction and the moving distance of the split bright line 311 corresponding to movement of the focusing lens 124, etc. in a certain direction with a certain distance.
[OCT Unit]

A configuration of the OCT unit 150 will be described with reference to FIG. 3. The OCT unit 150 has an optical system like that of a conventional Fourier-Domain-type optical image measuring device. That is to say, the OCT unit 150 has: an optical system that splits a low-coherence light into a reference light and a signal light, makes the signal light propagated through the eye and the reference light propagated through a reference object interfere with each other to generate an interference light, and detects this interference light to generate a detection signal. This detection signal is transmitted to the arithmetic and control unit 200.

A low-coherence light source 160 is a broadband light source that outputs a broadband low-coherence light L0. As this broadband light source, for example, a super luminescent diode (SLD), a light emitting diode (LED) and the like can be used.

For example, the low-coherence light L0 includes a light of a wavelength in the near-infrared region and has a temporal coherence length of about tens of micrometers. The low-coherence light L0 includes a longer wavelength than the illumination light of the retinal camera unit 1A (a wavelength of about 400-800 nm), for example, a wavelength in the range from about 800 to 900 nm.

The low-coherence light L0 outputted from the low-coherence light source 160 is led to an optical coupler 162 through an optical fiber 161. The optical fiber 161 is composed of, for example, a single mode fiber or a PM (polarization maintaining) fiber. The optical coupler 162 splits the low-coherence light L0 into the reference light LR and the signal light LS.

The optical coupler 162 has functions of both a part that splits the low-coherence light L0 into the reference light LR and the signal light LS (a splitter) and a part that superposes lights (a coupler), but will be idiomatically referred to as an "optical coupler" herein.

The reference light LR generated by the optical coupler 162 is led by an optical fiber 163 composed of a single mode fiber or the like, and is emitted from the end face of the fiber. Furthermore, the reference light LR is collimated by a collimator lens 171, propagated through a glass block 172, the polarizing plate ($\lambda/4$ plate) 175 and a density filter 173, and reflected by the reference mirror 174. The reference mirror is an example of a reference object of the present invention.

The reference light LR reflected by the reference mirror 174 is again propagated through the density filter 173, the polarizing plate 175 and the glass block 172, focused to the fiber end face of the optical fiber 163 by the collimator lens 171, and led to the optical coupler 162 through the optical fiber 163.

The glass block 172 and the density filter 173 act as a delaying part that makes the optical path lengths (the optical distances) of the reference light LR and the signal light LS match each other. Moreover, the glass block 172 and the density filter 173 act as a dispersion compensating part that makes the dispersion properties of the reference light LR and the signal light LS match each other.

Further, the density filter 173 acts as a neutral density filter that reduces the light amount of the reference light LR. The density filter 173 is composed of, for example, a rotary-type ND (Neutral Density) filter. The density filter 173 is driven to rotate by a driving mechanism that is not shown in the drawings, thereby changing the light amount of the reference light LR that contributes to generation of the interference light LD.

Moreover, the polarizing plate 175 is used in order to correct the optical path length of the reference light LR and is used in order to improve the image quality of the OCT image. The polarizing plate 175 is disposed by inclining, for example, approximately 3 degrees with respect to the direction perpendicular to the optical path direction of the reference light LR. The polarizing plate 175 is rotated and driven by a predefined driving mechanism, and the image quality of the coherent image is adjusted accordingly.

Figure 3:
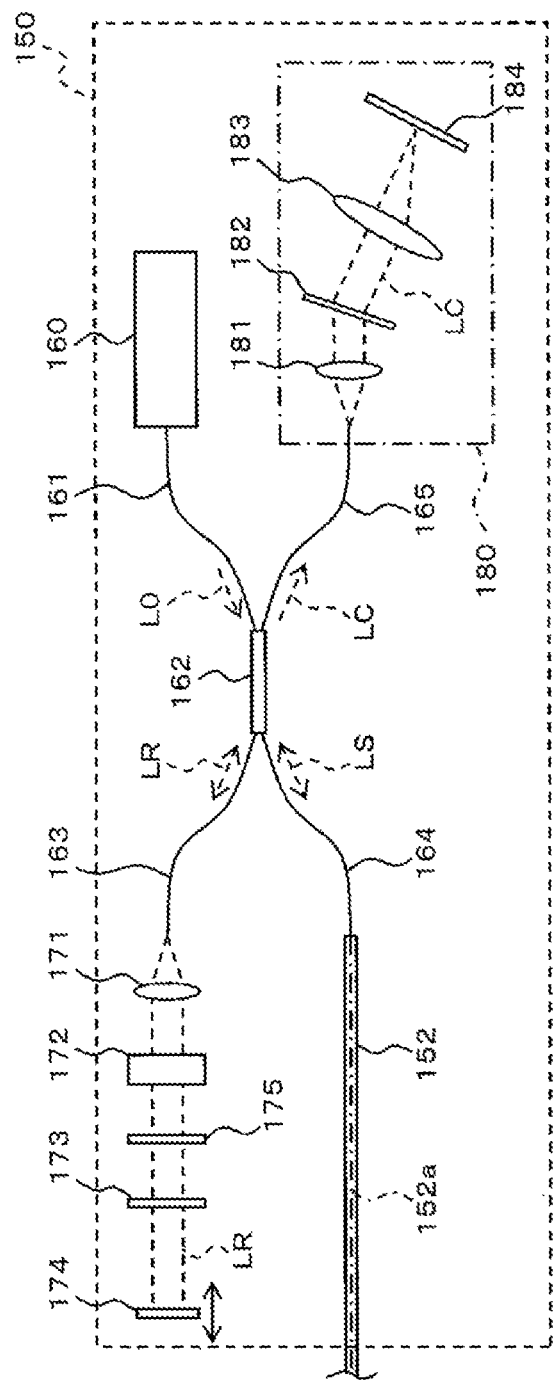
FIG. 3 is a schematic view showing an example of a configuration of an OCT unit in the embodiment of the optical image measuring device according to the present invention.

The reference mirror 174 is moved in the travelling direction (in the direction of the arrow on both sides, as shown in FIG. 3) of the reference light LR by the predefined driving mechanism. Accordingly, in response to the axial length of the subject's eye E and the working distance (the distance between the objective lens 113 and the subject's eye E), the optical path length of the reference light LR can be assured.

On the other hand, the signal light LS generated by the optical coupler 162 is led to the end of the connection line 152 through an optical fiber 164 composed of a single mode fiber or the like. The optical fiber 164 and the optical fiber 152a may be composed of one optical fiber, or may be integrally formed by joining the end faces of the respective fibers.

The signal light LS is led through the optical fiber 152a and guided to the retinal camera unit 1A. Furthermore, the signal light LS is propagated through the lens 142, the scan unit 141, the dichroic mirror 134, the imaging lens 126, the relay lens 125, the half mirror 190, the focusing lens 124, the imaging diaphragm 121, the aperture 112a of the aperture mirror 112 and the objective lens 113, and radiated to the eye E and radiated to the fundus oculi Ef. When the signal light LS is radiated to the fundus oculi Ef, the barrier filters 122 and 123 are retracted from the optical path in advance. At this moment, the half mirror 190 may also be retracted from the optical path.

The signal light LS having entered the eye E forms an image and reflected at fundus oculi Ef. At this moment, the signal light LS is not only reflected at the surfaces of the fundus oculi Ef but also scattered at a refractive index boundary of the deep part of fundus oculi Ef. Therefore, the signal light LS propagated through the fundus oculi Ef includes information that reflects the morphology of the surface of the fundus oculi Ef, and information that reflects a state of back scatter at the refractive index boundary of the deep tissues of the fundus oculi Ef. This light may be simply called as a fundus oculi reflected light of the signal light LS.

The fundus oculi reflected light of the signal light LS is guided reversely on the same path as the signal light LS travelling to the eye E, and focused to the end face of the optical fiber 152a. Moreover, the fundus oculi reflected light of the signal light LS enters the OCT unit 150 through the optical fiber 152a, and returns to the optical coupler 162 through the optical fiber 164.

The optical coupler 162 makes the signal light LS having returned through the fundus oculi Ef interfere with the reference light LR having returned after reflected by the reference mirror 174 to generate the interference light LC. The interference light LC is led to a spectrometer 180 through an optical fiber 165 composed of a single mode fiber or the like.

The spectrometer 180 detects the spectral components of the interference light LC. The spectrometer 180 includes a collimator lens 181, a diffraction grating 182, an imaging lens 183, and a CCD 184. The diffraction grating 182 may be either a transmission-type or a reflection-type. Moreover, it is also possible to use another photodetecting device (a line sensor or an area sensor) such as a CMOS, instead of the CCD 184.

The interference light LC having entered the spectrometer 180 is collimated by the collimator lens 181, and divided into spectra by the diffraction grating 182 (spectral resolution). The divided interference light LC is formed into an image on the image pick-up face of the CCD 184 by the imaging lens 183. The CCD 184 detects the respective spectral components of the divided interference light LC and converts the components into electric charges. The CCD 184 accumulates these electric charges and generates detection signals. Furthermore, the CCD 184 transmits these detection signals to the arithmetic and control unit 200.

Although a Michelson-type interferometer is employed in this embodiment, it is possible to employ any type of interferometer such as a Mach-Zehnder-type as necessary.

[Arithmetic and Control Unit]

A configuration of the arithmetic and control unit 200 will be described. The arithmetic and control unit 200 analyzes the detection signals inputted from the CCD 184, and forms an OCT image of the eye E. An arithmetic process for forming an OCT image is like that of a conventional Fourier-Domain-type OCT device.

Further, the arithmetic and control unit 200 controls each part of the retinal camera unit 1A and the OCT unit 150.

As control of the retinal camera unit 1A, the arithmetic and control unit 200 executes: control of output of the illumination lights by the observation light source 101 and the imaging light source 103; control of insertion/retraction of the exciter filters 105, 106 and the barrier filters 122, 123 to/from the optical path; control of the operation of a display device such as the LCD 140; control of movement of the illumination diaphragm 110 (control of the aperture value); control of the aperture value of the imaging diaphragm 121; control of movement of the focusing lens 124 (adjustments of focus and magnification); control of the focusing optical system and the alignment optical system 109A and so on. Furthermore, the arithmetic and control unit 200 controls the scan unit 141 to scan with the signal light LS.

Further, as control of the OCT unit 150, the arithmetic and control unit 200 executes: control of output of the low-coherence light L0 by the low-coherence light source 160; control of movement of each of the reference mirror 174; control of the rotation operation of the density filter 173 (an operation to change the reduction amount of the light amount of the reference light LR); control of a time for electric charge accumulation, the timing for electric charge accumulation and the timing for signal transmission by the CCD 184; and so on.

The arithmetic and control unit 200 includes a microprocessor, a RAM, a ROM, a hard disk drive, a keyboard, a mouse, a display, a communication interface, and so on, as in conventional computers. The hard disk drive stores a computer program for controlling the optical image measuring device 1. Moreover, the arithmetic and control unit 200 may be provided with a circuit board dedicated for forming OCT images based on detection signals from the CCD 184.

[Control System]

Figure 5:
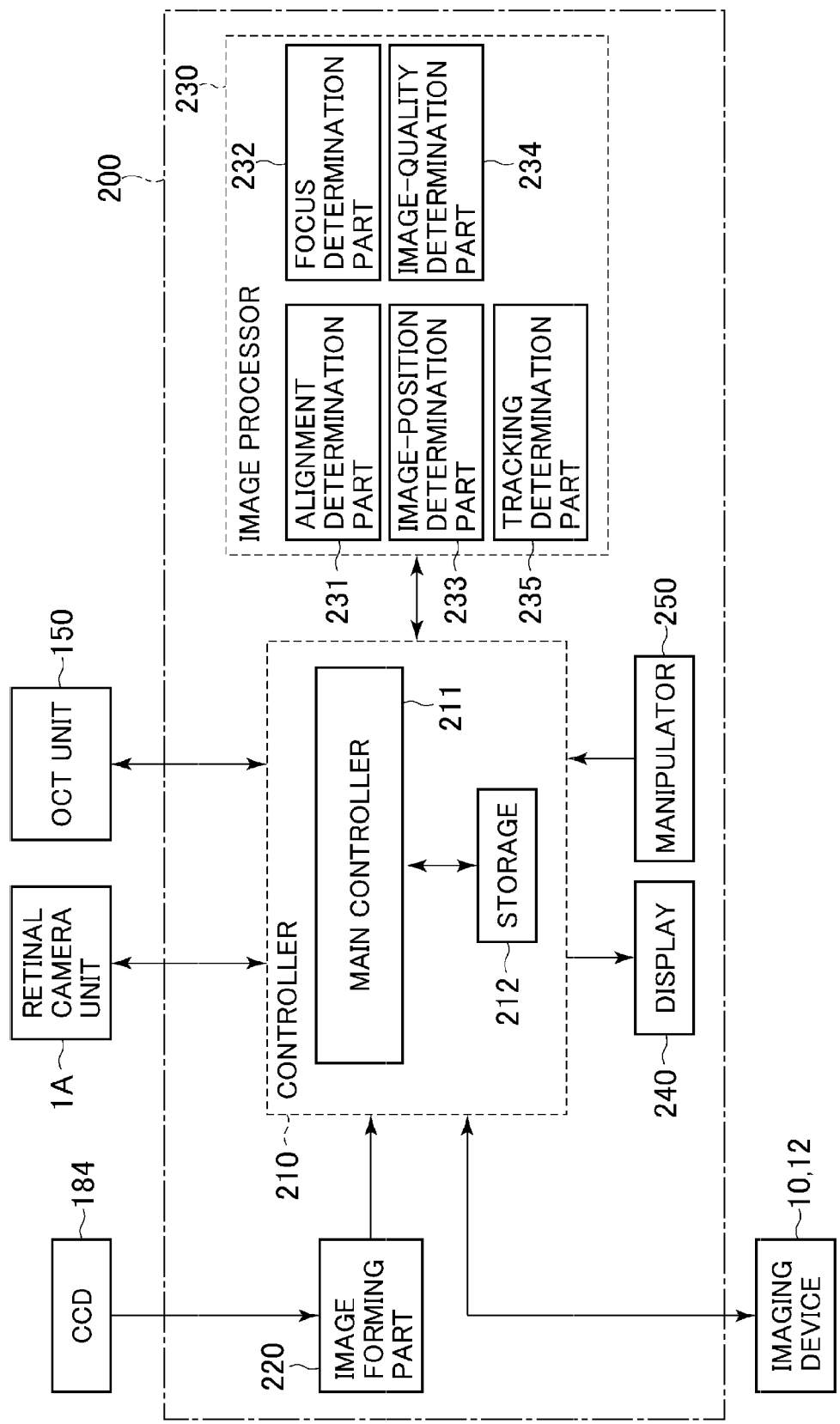
FIG. 5 is a schematic block diagram showing an example of a configuration of a control system of the embodiment of the optical image measuring device according to the present invention.

A configuration of a control system of the optical image measuring device 1 will be described with reference to FIG. 5. In FIG. 5, the imaging device 10 and 12 and the retinal camera unit 1A are separately described, and the CCD 184 and the OCT unit 150 are separately described. However, as explained above, the imaging device 10 and 12 are provided in the retinal camera unit 1A, and the CCD 184 is provided in the OCT unit 150.

(Controller)

The control system of the fundus oculi observing device 1 has a configuration centered on a controller 210. The controller 210 includes, for example, the aforementioned microprocessor, RAM, ROM, hard disk drive, and communication interface. The controller 210 is an example of a control part of the present invention.

The controller 210 is provided with a main controller 211 and a storage 212. The main controller 211 controls each part of the retinal camera unit 1A, the OCT unit 150 and the arithmetic and control unit 200.

The storage 212 stores various kinds of data. The data stored in the storage 212 is, for example, image data of OCT images, image data of fundus oculi images Ef', and eye information. The eye information includes various information on the eye, for example, information on a subject such as a patient ID and a name, information on identification of left eye or right eye, and diagnostic result and examination result of the eye. The main controller 211 executes a process of writing data into the storage 212, and a process of reading out the data from the storage 212.

Furthermore, data for the unit moving distance (described above) for the alignment adjustment and focus adjustment is stored in the storage 212. Moreover, a computer program for executing an action (flow chart), which is described below, is stored in the storage 212. The main controller 211 operates based on the data and the computer program.

(Image Forming Part)

An image forming part 220 forms image data of a tomographic image of the fundus oculi Ef based on the detection signals from the CCD 184. Like the conventional Fourier-Domain OCT technique, this image data forming process includes processes such as noise elimination (noise reduction), filtering, and FFT (Fast Fourier Transform).

The image forming part 220 includes, for example, the aforementioned circuit board and communication interface. The image forming part 220 is an example of an image forming part of the present invention. In this specification, "image data" may be identified with an "image" presented based on the image data.

(Image Processor)

An image processor 230 executes various image processing and analysis on fundus oculi images (photographs of a retinal surface) obtained by the retinal camera unit 1A and images formed by the image forming part 220. For example, the image processor 230 executes various correction processes such as luminance correction and dispersion correction of images.

Further, the image processor 230 executes, for example, an interpolation process of interpolating pixels between tomographic images formed by the image forming part 220, thereby forming image data of a three-dimensional image of the fundus oculi Ef.

Image data of a three-dimensional image refers to image data that the positions of pixels are defined by the three-dimensional coordinates. The image data of a three-dimensional image is, for example, image data composed of three-dimensionally arranged voxels. This image data is referred to as volume data, voxel data, or the like. For displaying an image based on the volume data, the image processor 230 executes a rendering process (such as volume rendering and MIP (Maximum Intensity Projection)) on this volume data, and forms image data of a pseudo three-dimensional image taken from a specific view direction. On a display device such as the display 240, this pseudo three-dimensional image is displayed.

Further, it is also possible to form stack data of a plurality of tomographic images as the image data of a three-dimensional image. Stack data is image data obtained by three-dimensionally arranging a plurality of tomographic images obtained along a plurality of scanning lines, based on the positional relation of the scanning lines. That is to say, stack data is image data obtained by expressing a plurality of tomographic images defined by originally individual two-dimensional coordinate systems by a three-dimensional coordinate system (namely, embedding into a three-dimensional space). The image processor 230 is capable of executing various image processing and analysis on three-dimensional images.

An alignment determination part 231, a focus determination part 232, an image-position determination part 233, an image-quality determination part 234, and a tracking determination part 235 are provided in the image processor 230. These determination parts 231 to 235 respectively constitute a part of the "determining part" of the present invention.

The alignment determination part 231, at the predefined timing after the alignment adjustment of the optical system, determines the suitability of the position of the optical system, that is, it determines whether or not the optical system is disposed at the appropriate position with respect to the subject's eye E. In this way, the alignment determination part 231 determines the suitability of the alignment state at the predefined timing after the alignment adjustment. Moreover, this type of alignment determination is effective even after the alignment adjustment because the alignment state may change resulting from eye movement of the subject's eye E, movement of the subject, etc.

Examples of the processing performed by the alignment determination part 231 are explained. The alignment determination part 231 analyzes the fundus oculi image of the subject's eye E that is obtained in the state in which the alignment bright points 310 are projected after the alignment adjustment (refer to FIG. 4). Here, the position of the alignment scale 309 in the frame of the fundus oculi image is already known.

First, the alignment determination part 231 specifies the positions (the position of the center of gravity, etc.) of the pair of alignment bright points 310, in the manner described above. Next, the alignment determination part 231 determines whether these specific positions are within the predetermined allowable range, that is, it determines whether they are within the alignment scale 309 (bracket shaped image). If it is determined that these specific positions are within the allowable range, the alignment determination part 231 determines that the alignment state is appropriate. On the other hand, for cases in which these specific positions are not within the allowable range, the alignment determination part 231 determines that the alignment state is not appropriate. Moreover, specific examples of the processing that determines the suitability of the alignment state are, for example, described in Japanese patent application 2008-13989 submitted by the present applicant.

At the predefined timing after the focus adjustment, the focus determination part 232 determines the suitability of the focus state, that is, it determines whether or not focus is being conducted appropriately with respect to the fundus oculi Ef (whether or not they are brought into focus). This type of alignment determination is effective even after the focus adjustment because the focus state may change resulting from eye movement of the subject's eye E, movement of the subject, etc.

Examples of the processing performed by the focus determination part 232 are explained. The focus determination part 232 analyzes the fundus oculi image of the subject's eye E that is obtained in the state in which the split bright lines 311 are projected after the focus adjustment (refer to FIG. 4).

First, the focus determination part 232 specifies the positions (the position of the center of gravity) in the lateral direction of the vertical split bright lines 311. Next, the focus determination part 232 determines whether these specific positions are within the allowable range in the lateral direction. This allowable range is previously set. Accordingly, it is determined whether or not the vertical split bright lines 311 are disposed along a substantially straight line. For cases in which it is determined that these specific positions are within the allowable range, the focus determination part 232 determines that the focus state is appropriate. On the other hand, for cases in which these specific positions are not within the allowable range, the focus determination part 232 determines that the focus state is not appropriate. Moreover, specific examples of the processing that determines the suitability of the focus state are, for example, described in the Japanese patent application 2008-13989 submitted by the present applicant.

The image-position determination part 233 determines the suitability of the position of the tomographic image of the fundus oculi Ef in the frame. Particularly, the image-position determination part 233 determines the suitability of the depth position (the position in the z direction) of the tomographic image in the frame.

The tomographic image is generally obtained after alignment adjustment and focus adjustment are executed; as a result, the image corresponding to the retinal surface is displayed in the frame. The image-position determination part 233 specifies the position of the image corresponding to the retinal surface in the frame in the z direction. Specific examples of this processing are explained.

The tomographic image is constituted from a plurality of one-dimensional images that stretch in the depth direction. These one-dimensional images are disposed along the scanning lines of the signal light LS. Moreover, the frame of the tomographic image is black (brightness value 0), and the pixels corresponding to the tissue (layer) of the fundus oculi are of a brightness value corresponding to the intensity of the reflection light from the region. The region at the depth not reached by the signal light LS is expressed in black color. That is, the tomographic image is the image in which various layers of the fundus oculi are expressed in a gray scale inside the black frame. Moreover, the tomographic image may be a pseudo-color image corresponding to the brightness value.

First, the image-position determination part 233 specifies the pixels corresponding to the retinal surface, based on the brightness value of the pixels constituting the above respective one-dimensional image. Accordingly, a group of pixels disposed along the scanning direction of the signal light LS is specified. This pixel group is the image area corresponding to the retinal surface. Moreover, the specific target is not limited to the retinal surface and may, for example, be a region with high luminance such as IS/OS.

Next, the image-position determination part 233 determines whether the specified pixel group falls within the allowable range in the z direction. This allowable range is previously set. For cases in which the pixel group falls within the allowable range, the image-position determination part 233 determines that the depth position of the tomographic image in the frame is appropriate. On the other hand, for cases in which the pixel group does not fall within the allowable range, the image-position determination part 233 determines that the depth position of the tomographic image in the frame is not appropriate.

Moreover, position determination of the tomographic image may be performed such that the upper end area (the image area corresponding to the retinal surface) and the lower end area (the image area corresponding to the furthest reaching depths of the signal light LS) of the tomographic image are included in the frame, that is, such that the upper end area and the lower end area are not cut from the frame. In order to achieve this, for example, it may be constituted such that, for each one-dimensional image, it is determined whether or not the brightness values of the upper vicinity area and the lower vicinity area of the frame is 0, and furthermore, it is determined whether or not a pixel group with a brightness value not equal to 0 is present.

The image-quality determination part 234 analyzes the tomographic image of the fundus oculi Ef, and determines the suitability of the image quality of the tomographic image. There are various evaluation methods for image quality; however, one example is explained below.

First, the image-quality determination part 234 specifies pixels with the maximum brightness and pixels with the minimum brightness with regard to each one-dimensional image in the depth direction constituting the tomographic image. Next, the image-quality determination part 234 creates a histogram for the brightness value (for example, the histogram of 8 bits), based on the brightness values of the pixel group (for example, approximately 40 pixels) in the predefined range, including each pixel that is specified.

Next, the image-quality determination part 234 searches for the maximum position (brightness value) with a frequency exceeding 0 for the histogram corresponding to the pixel group, including pixels of the minimum brightness. Furthermore, for the histogram corresponding to the pixel group, including pixels with the maximum brightness, the total pixel number (N) that is included in the range below the brightness value that is searched above, and a total pixel number (S) that is included in the 255th brightness value from the top based on the searched brightness value are calculated. Moreover, the image-quality determination part 234 evaluates what % of the whole corresponds to parts that can be treated as signals (that is, parts treated as not being noise) in the tomographic image, using the following calculation formula: $100 \times S \div (S+N)$. This type of arithmetic processing is executed for each one-dimensional image, and the mean value of these arithmetic results is used as an evaluation value of the image quality.

The image-quality determination part 234 determines whether the evaluation value obtained in this way is more than a predefined threshold. This threshold is previously set. For cases in which it is determined that the evaluation value is equal to or more than the threshold, the image-quality determination part 234 determines that the image quality is appropriate. On the other hand, for cases in which it is determined that the evaluation item is below the threshold, the image-quality determination part 234 determines that the image quality is not appropriate.

The tracking determination part 235 determines the suitability of the tracking state, while tracking of the irradiation position of the signal light LS is being executed with respect to the region of interest (the acquisition target area of the OCT image) of the fundus oculi Ef. That is, the tracking determination part 235 determines whether or not tracking of the irradiation position of the signal light LS is being executed appropriately, with respect to the eye movement of the subject's eye E.

Moreover, tracking can be executed by controlling the galvano mirror in the scan unit 141. For example, for cases in which tracking is performed based on the fundus oculi image (motion picture), it specifies the position of a characteristic region of the fundus oculi (optic papilla, etc.) in the respective frames of the motion picture, and controls the irradiation position of the signal light LS such that this specific position is located at the same position (for example, in the center area of the frame, etc.) during the measurement.

Moreover, for cases in which tracking is performed based on the OCT image, it repeatedly applies a predefined scanning pattern (for example, a cross scan), and based on a characteristic shape (for example, a concave shape of the macula) depicted in the sequentially obtained pair of tomographic images, it controls the irradiation position of the signal light LS such that the characteristic point (for example, the macular center) is located at the same position (for example, in the center area of the frame, etc.) during the measurement.

Moreover, for cases in which OCT measurement is performed, since there is a possibility of the accuracy becoming insufficient with tracking using the fundus oculi image, it is desirable that tracking based on the OCT image be performed. Moreover, for the fundus oculi image, compared to the optic papilla, it is difficult to specify the position of the macula; hence, especially for cases in which the OCT image of the macula is obtained, it is desirable that tracking using the OCT image be performed.

The target regions for the OCT measurement are set by selecting an internal fixation target (the macula, optic papilla, etc.). The tracking determination part 235 determines the suitability of the tracking state, for example, by determining whether or not the tracking target region is included in the scan area of the signal light LS.

Moreover, the scan area is set, for example, in a predefined area (a 6 mm×6 mm square area, etc.) whose center is on the optical axis of the imaging optical system 120. Moreover, the position of the tracking target region is obtained with high accuracy, for example, with tracking using the above OCT images.

The signal light LS is irradiated to the subject's eye E, along the same optical axis as the illumination light of fundus photography (the optical axis of the imaging optical system 120), and the fundus oculi reflection light is also guided along the optical axis. Therefore, by setting the center of the scan area of the signal light LS on the optical axis, the center of the frame of the fundus oculi image and the center position of the scan area match each other. By utilizing this, it is possible to display the image showing the position of the scan area and the image showing the position of the tracking target region, on the fundus oculi image (described later).

The image processor 230 includes, for example, the aforementioned microprocessor, RAM, ROM, hard disk drive, and circuit board. Moreover, the image processor 230 may include dedicated circuit boards that execute a predetermined image processing and analysis processing.

(The Display and the Manipulator)

The display 240 is constituted by including the touch panel monitor 11. Furthermore, the display of the arithmetic and control unit 200, etc., may also be included in the display 240. The display 240 is one example of "the display part" of the present invention. The manipulator 250 is constituted by including input devices and operation devices, such as a keyboard and a mouse. Moreover, various input devices and operation devices that are provided on the housing surface and on the external sections of the optical image measuring device 1 are included in the manipulator 250.

The display 240 and the manipulator 250 do not need to be composed as separate devices. For example, like a touch panel LCD, a device in which the display 240 and the manipulator 250 are formed in one body can be used.

[Scan with Signal Light and Image Processing]

A scan with the signal light LS and an OCT image will be described.

The scan aspect of the signal light LS by the optical image measuring device 1 is, for example, a horizontal scan, vertical scan, cruciform scan, radial scan, circular scan, concentric scan, and helical scan. These scan aspects are selectively used as necessary in consideration of an observation site of the fundus oculi, an analysis target (the retinal thickness or the like), a time required to scan, the accuracy of a scan, and so on.

A horizontal scan is a scan with the signal light LS in the horizontal direction (x-direction). The horizontal scan includes an aspect of scanning with the signal light LS along a plurality of scanning lines extending in the horizontal direction arranged in the vertical direction (y-direction). In this aspect, it is possible to set any interval between scanning lines. By setting the interval between scanning lines to be sufficiently narrow, it is possible to form the aforementioned three-dimensional image (three-dimensional scan). A vertical scan is also performed in a similar manner.

A cruciform scan is a scan with the signal light LS along a cross-shape trajectory formed by two linear trajectories (line trajectories) orthogonal to each other. A radial scan is a scan with the signal light LS along a radial trajectory formed by a plurality of line trajectories arranged at predetermined angles. The cruciform scan is an example of the radial scan.

A circular scan is a scan with the signal light LS along a circular trajectory. A concentric scan is a scan with the signal light LS along a plurality of circular trajectories arranged concentrically around a predetermined center position. The circular scan is regarded as a special example of the concentric scan. A helical scan is a scan with the signal light LS along a helical trajectory.

With the configuration as described before, the scan unit 141 is capable of scanning with the signal light LS in the x-direction and the y-direction, respectively, and is therefore capable of scanning with the signal light LS along any sort of trajectory on the xy-plane. Thus, it is possible to realize various types of scan aspects as described above.

By scanning the signal light LS in the mode described above, for each scanning point (irradiation position), a one-dimensional image that extends in the depth direction is obtained, and by arranging these one-dimensional images along scanning lines (scan trajectory), it is possible to form a two-dimensional tomographic image extends both the direction of the scanning lines and the depth direction (z direction). Moreover, in a case that the interval between scanning lines is narrow, it is possible to form the aforementioned three-dimensional image.

[Operation]

Figure 6:
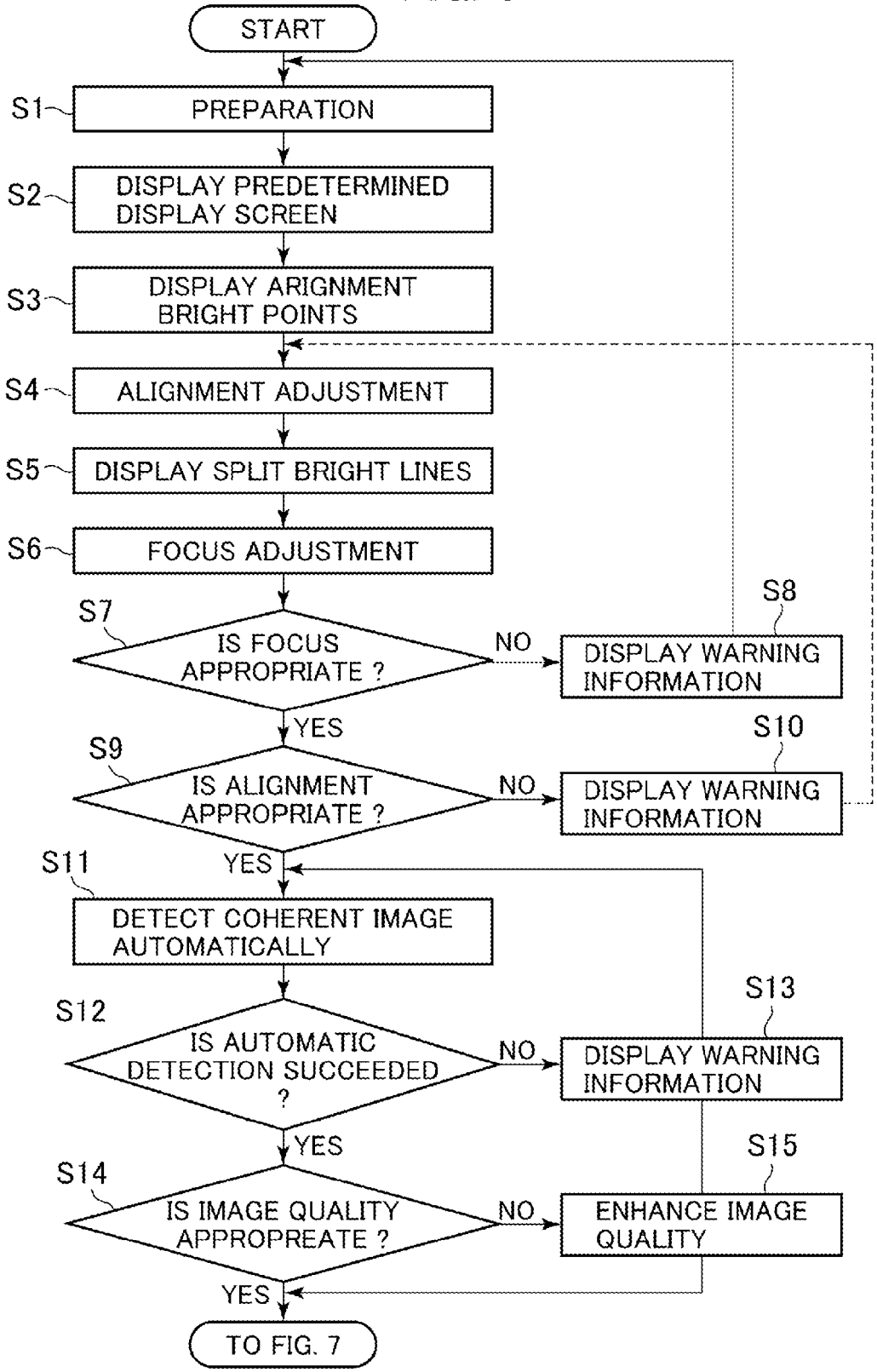
FIG. 6 is a flow chart showing an example of an operation of the embodiment of the optical image measuring device according to the present invention.
Figure 7:
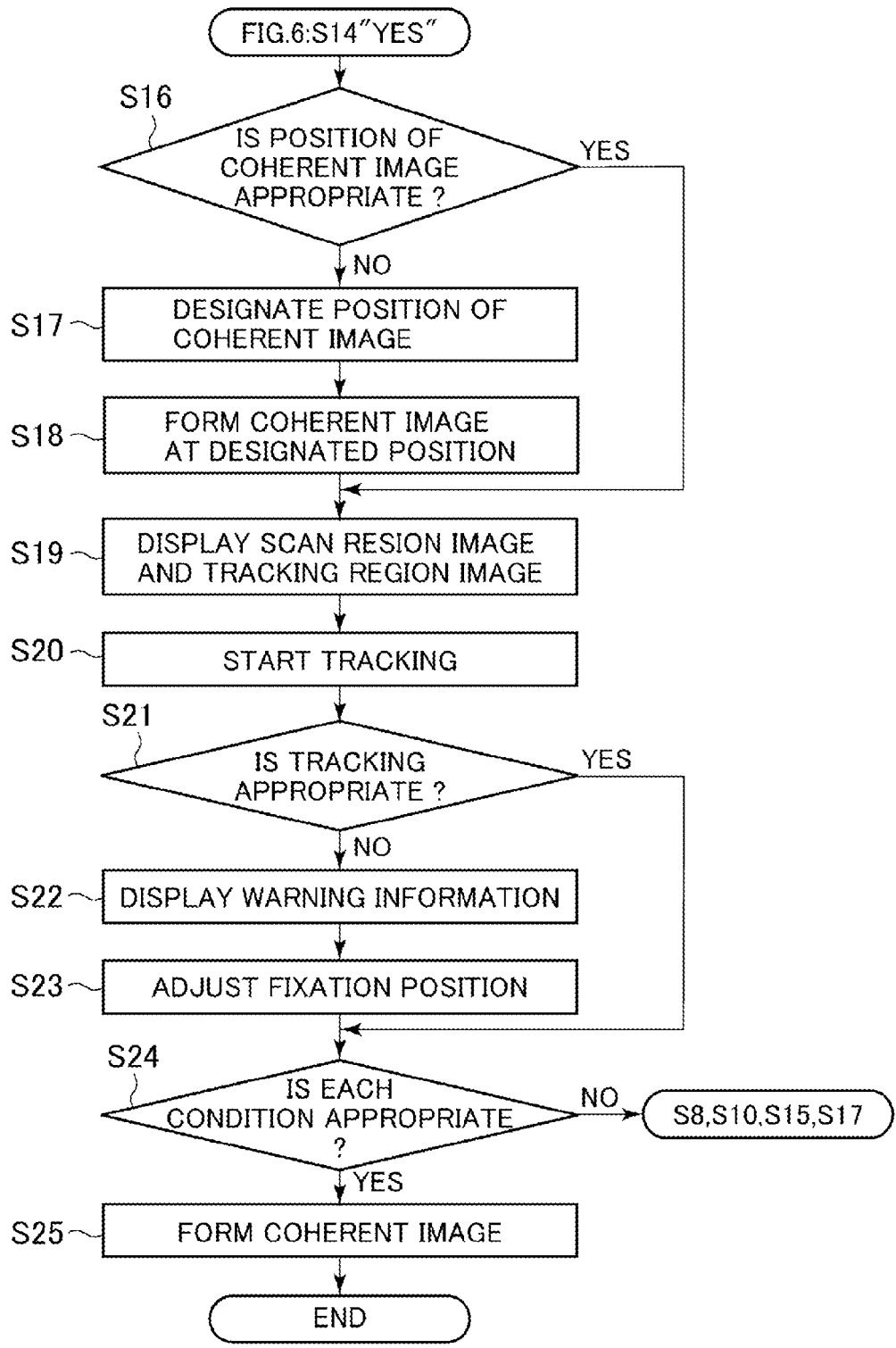
FIG. 7 is a flow chart showing an example of an operation of the embodiment of the optical image measuring device according to the present invention.

An operation of the optical image measuring device 1 will be described. A flow chart shown in FIG. 6 and FIG. 7 represent an example of the operation of the optical image measuring device 1.

First, in the same way as with normal photographing of the fundus oculi, preparations for examination are performed as follows (S1). The face of the subject is positioned in contact with the chin rest and the forehead placement, and the subject's eye E is directly opposite the retinal camera unit 1A.

Figure 8:
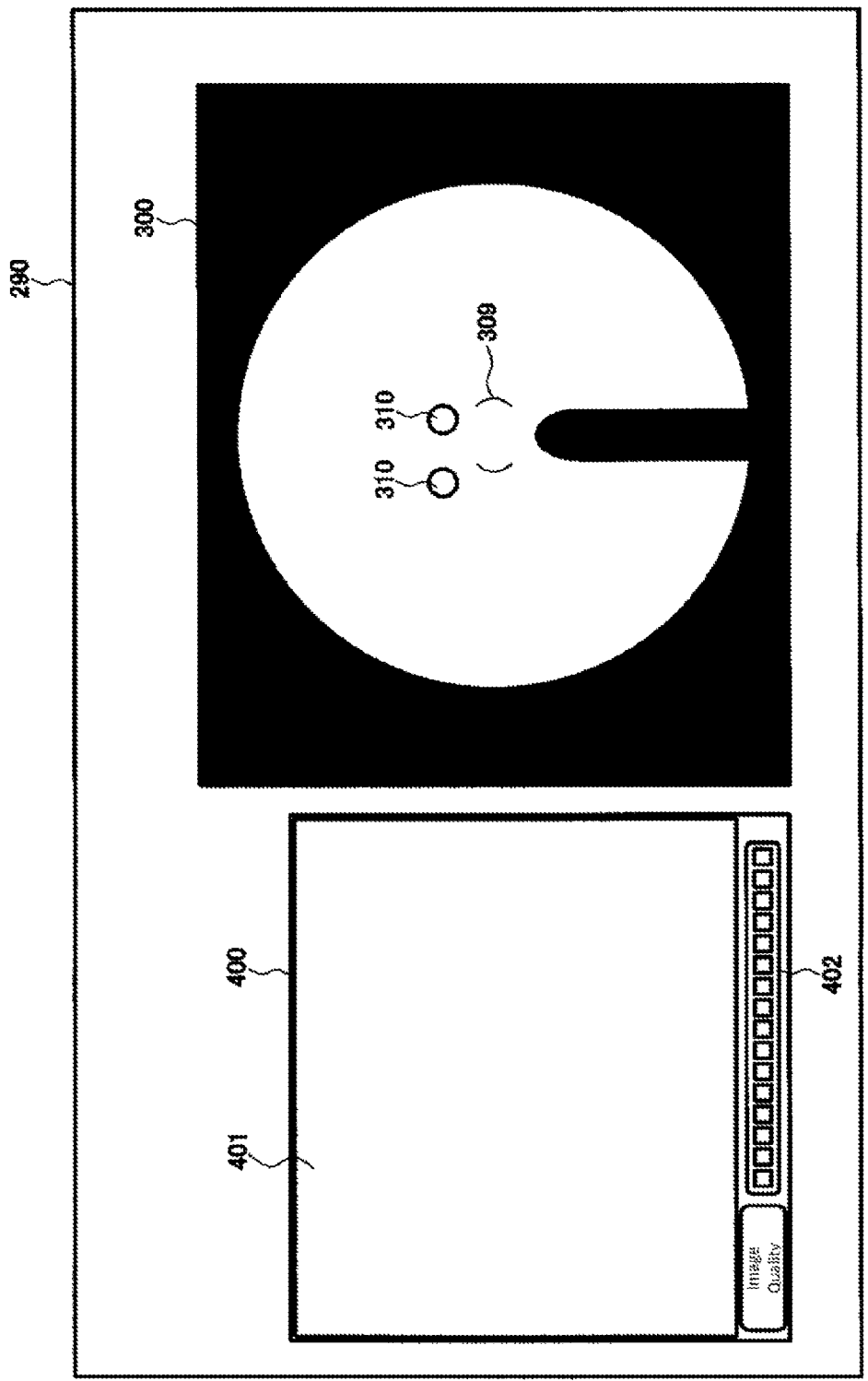
FIG. 8 is a schematic view showing an example of a configuration of a display screen in the embodiment of the optical image measuring device according to the present invention.

In response to a prescribed operation (for example, the operation to turn on the power), the controller 210 causes the display 240 (touch panel monitor 11) to display a predetermined display screen (for example, the display screen 290 shown in FIG. 8) (S2). The display screen 290 includes an adjustment screen 300 and a coherent image display screen 400. The adjustment screen 300 is similar to the screen shown in FIG. 4, and is used for alignment adjustment and focus adjustment. Although it is not shown in the diagrams, on the adjustment screen 300, images captured by the retinal camera unit 1A are displayed. Moreover, in FIG. 8 to FIG. 12, and in FIG. 15, among the information shown in FIG. 4, information not needed for the following explanation has been omitted. On the coherent image display screen 400, coherent images are displayed (as described later), but the display state at this stage is, for example, a "sandstorm" state (that is, no image is displayed on it).

The examiner operates the manipulator 250, and lights up the observation light source 101. In this way, the anterior eye image of the subject's eye E is displayed on the adjustment screen 300. The examiner operates the manipulator 250 (control lever), and moves the retinal camera unit 1A toward the subject. At this time, the display image on the adjustment screen 300 is switched to an observation image of the fundus oculi.

Figure 9:
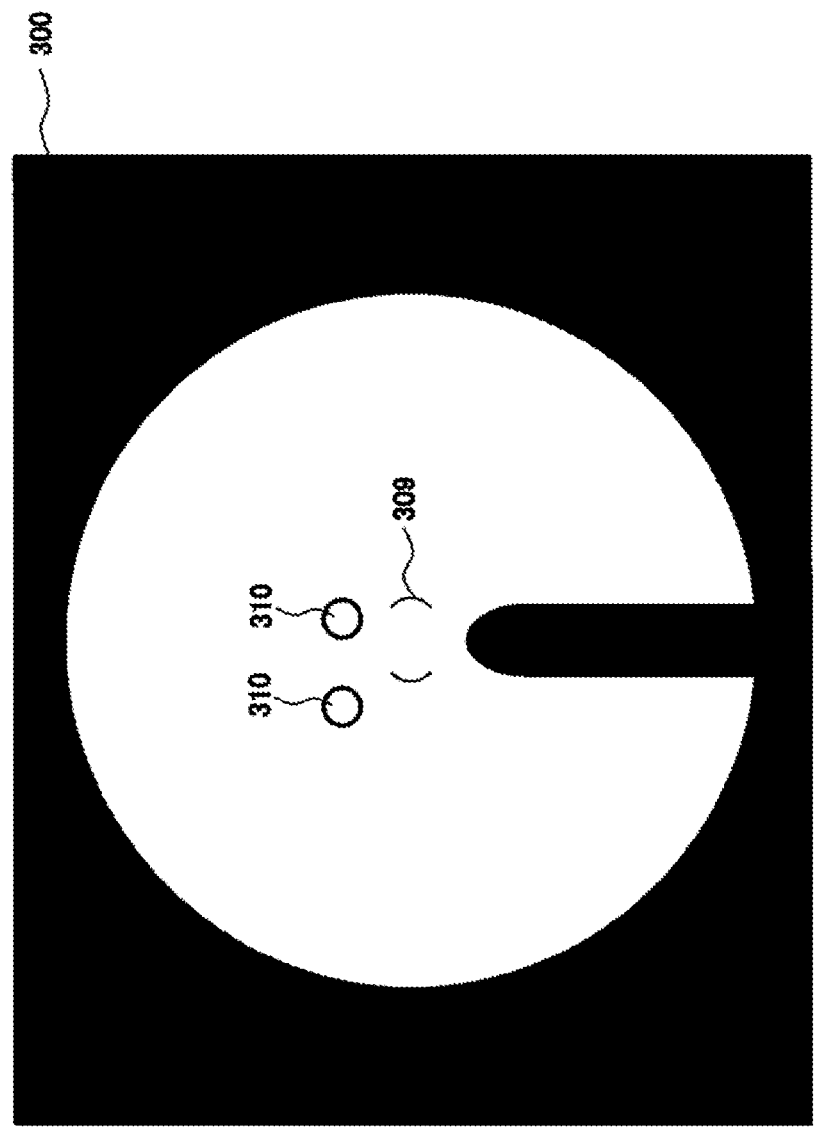
FIG. 9 is a schematic view showing an example of a configuration of a display screen in the embodiment of the optical image measuring device according to the present invention.

In response to a prescribed operation, the controller 210 lights up the alignment light source 190a. In this way, the alignment bright points are projected on to the subject's eye E, and as shown in FIG. 9, the alignment bright points 310 are displayed on the adjustment screen 300 (S3). At this stage, generally the alignment state is unsuitable, so two alignment bright points 310 are displayed on the exterior of the alignment scale 309.

Figure 10:
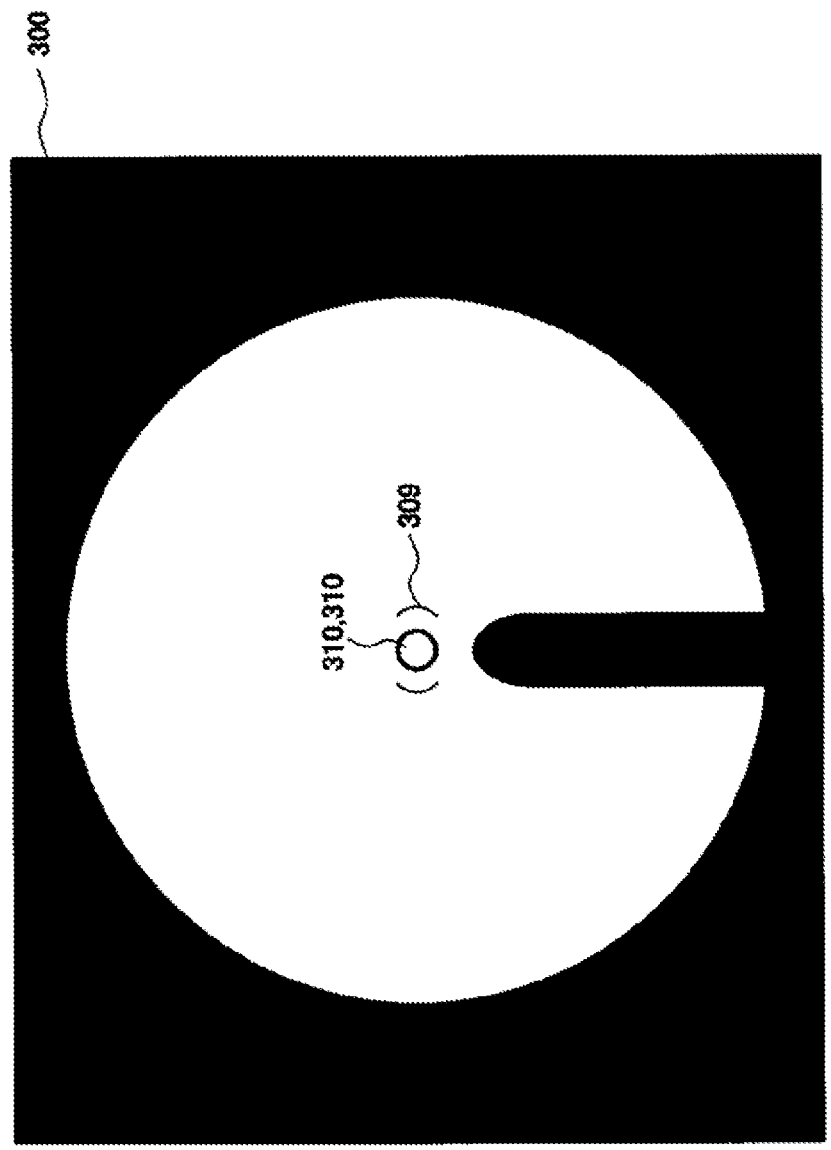
FIG. 10 is a schematic view showing an example of a configuration of a display screen in the embodiment of the optical image measuring device according to the present invention.

The examiner operates the control lever and adjusts the position of the retinal camera unit 1A so as to move the two alignment bright points 310 to the interior of the alignment scale 309 (S4). The adjustment screen 300, in a state such that the alignment adjustment is completed, is shown in FIG. 10. Moreover, instead of manually performing the alignment adjustment in this manner, as described above, it is also possible to perform auto-alignment.

Figure 11:
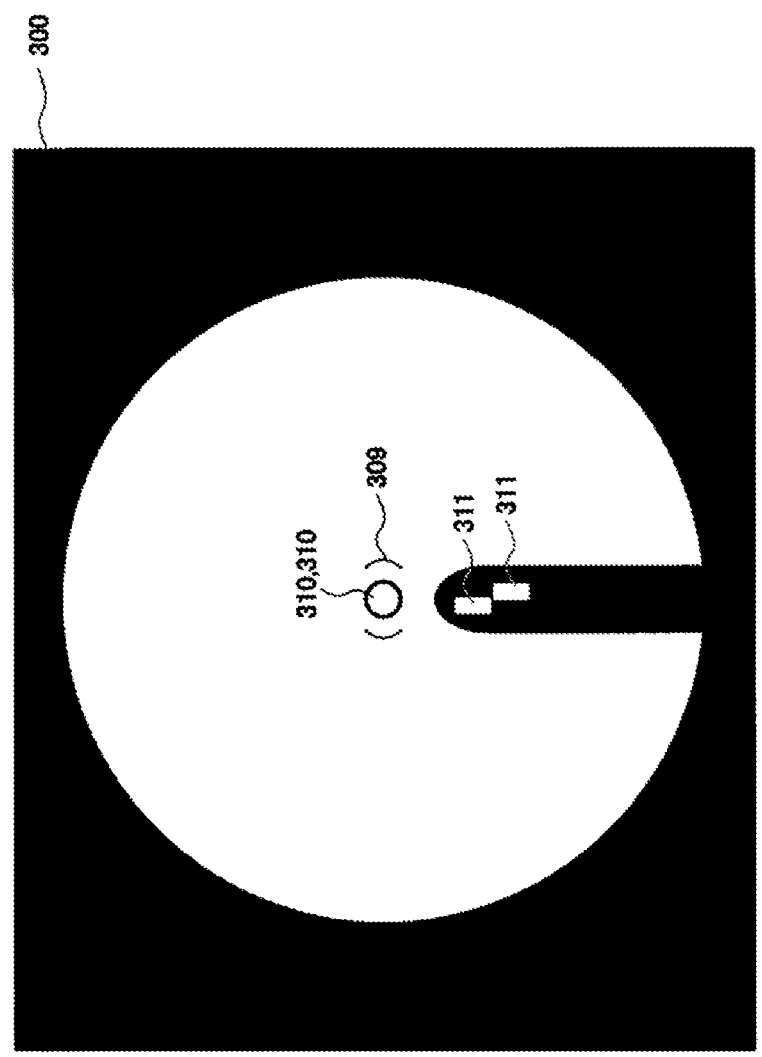
FIG. 11 is a schematic view showing an example of a configuration of a display screen in the embodiment of the optical image measuring device according to the present invention.

When the alignment adjustment is completed, the focus adjustment is performed. For this purpose, the controller 210 lights up LED 109a. In this way, the split bright lines are projected on to the subject's eye E, and as shown in FIG. 11, the split bright lines 311 are displayed on the adjustment screen 300 (S5). At this stage, generally the state of the focus is unsuitable, so the split bright lines 311 above and below do not form one straight line. The controller 210, in the manner above, performs the autofocus (S6). The focus determination part 232 determines the suitability of the state of the focus obtained from the autofocus (S7).

If the state of the focus is determined to be inappropriate, (for example, if the autofocus has failed) (S7: No), the controller 210 displays the prescribed warning information on the display 240 (S8). This warning information state, for example, a message indicating that the autofocus has failed, or a message indicating that redoing the examination is recommended. The warning information may be character string information, or it may be image information. A message such as the following is an example of character string information: "The autofocus has failed. Please pull the control lever once again, and redo the examination." The examiner, who is aware that the autofocus has failed by means of the warning information, redoes the examination from the beginning. Furthermore, if in Step 7, "No" occurs a prescribed number of times, the examination may be terminated.

Figure 12:
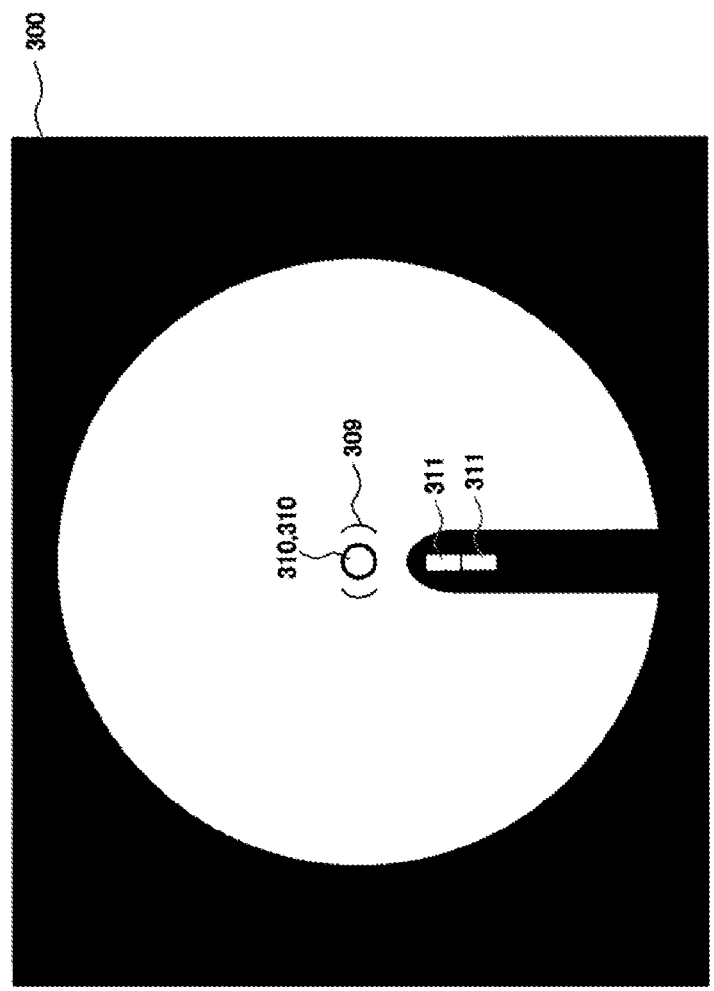
FIG. 12 is a schematic view showing an example of a configuration of a display screen in the embodiment of the optical image measuring device according to the present invention.

If the autofocus is successful (S7: Yes), the split bright lines 311 above and below, which are displayed on the adjustment screen 300, are arranged in one straight line, as shown in FIG. 12. The alignment determination part 231, based on the positions of the alignment bright points 310 at this stage, determines the suitability of the alignment state (S9).

If it is determined that the alignment state is not suitable (S9: No), the controller 210 displays the prescribed warning information on the display 240 (S10). This warning information states, for example, a message indicating that the alignment state has become worse, or a message indicating that redoing the alignment is recommended. The warning information may be character string information, or it may be image information. A message such as the following is an example of character string information: "Superpose the alignment bright points each other, and move them inside the scale." The examiner, who is aware that the alignment state is inappropriate by means of the warning information, returns to Step 4, and redoes the alignment. Furthermore, if in Step 9, "No" occurs a prescribed number of times, the examination may be terminated, or the examination may be redone from the beginning, etc.

If the alignment state is determined to be appropriate (S9: Yes), the controller 210 controls the OCT unit 150, the scan unit 141, an image forming part 220, etc., and performs automatic detection of the coherent image (the tomographic image) of the fundus oculi Ef (S11). The automatic detection is performed, for example, by moving the reference mirror 174 and analyzing the detected signals obtained. Moreover, the automatic detection may be performed by actually forming a coherent image, and analyzing the luminance values of this coherent image.

If the automatic detection fails (S12: No), the controller 210 displays the prescribed warning information on the display 240 (S13). This warning information states, for example, a message indicating that the coherent image was not detected, or a message indicating that redoing the automatic detection is recommended. The warning information may be character string information, or it may be image information. A message such as the following is an example of character string information: "Automatic detection of a coherent image has failed. Please do it again." The examiner, who is aware that the automatic detection has failed by means of the warning information, performs a prescribed operation (for example, touching the screen of a touch panel monitor 11), and instructs to redo the automatic detection of the coherent image. Furthermore, if in Step 12, "No" occurs a prescribed number of times, the examination may be terminated, or the examination may be redone from the beginning, etc.

Figure 13:
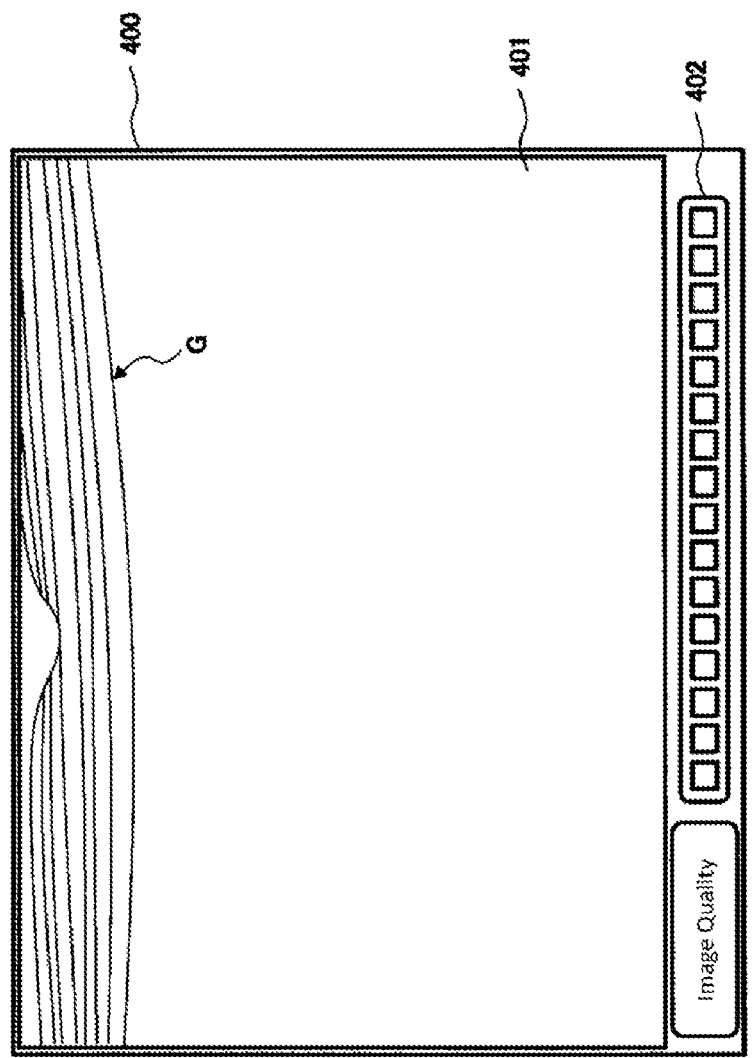
FIG. 13 is a schematic view showing an example of a configuration of a display screen in the embodiment of the optical image measuring device according to the present invention.

If the automatic detection is successful (S12: Yes), the coherent image of the fundus oculi Ef is depicted somewhere in the frame. The coherent image is displayed on the image display 401 of the coherent image display screen 400. The coherent image at this stage, as shown in FIG. 13, for example, is displayed at a position such that a part of it protrudes from the coherent image display screen 400.

The image-quality determination part 234 determines the suitability of the image quality of the detected coherent image (S14). If the image quality is determined to be inappropriate (S14: No), the controller 210 controls to rotate the polarizing plate 175 and raises the image quality level (S15). At this time, it is desirable to control the polarizing plate 175 so as to maximize the image quality level.

Furthermore, the image quality level is indicated on the image quality display 402 of the coherent image display screen 400. The image quality display 402 is an indicator showing the evaluated value of image quality. Moreover, the evaluated values may be displayed as is.

If the image quality level is determined to be appropriate (S14: Yes), the image position determination part 233 determines the suitability of the position of the coherent image within the frame (S16).

If part of a coherent image G is cut off from the frame as shown in FIG. 13, or if the coherent image G gets too close to the upper edge area or the lower edge area, the position of the coherent image G is determined to be inappropriate. At this time, warning information indicating this fact may be displayed.

If the position of the coherent image G is determined to be inappropriate (S16: No), the examiner designates a desired display position for the coherent image G within the frame (S17). This operation is performed by, for example, touching the desired position on the image display 401 (touch panel monitor 11). Moreover, the previously set position (for example, the center position of the image display 401) may also be automatically set.

Figure 14:
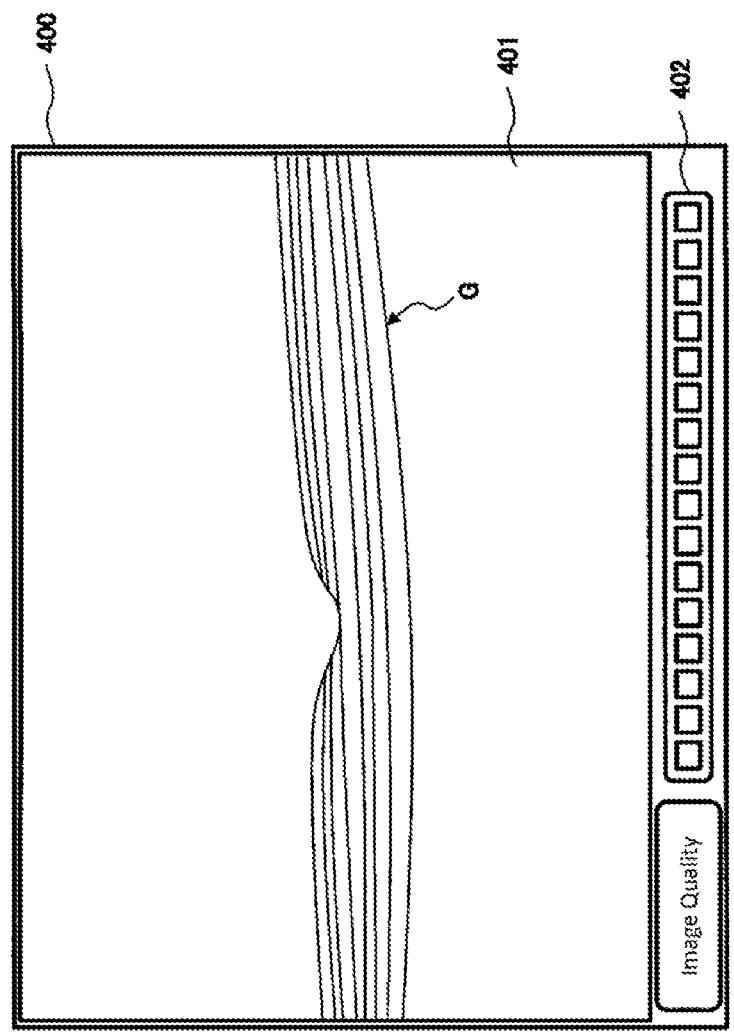
FIG. 14 is a schematic view showing an example of a configuration of a display screen in the embodiment of the optical image measuring device according to the present invention.

The controller 210 derives the displacement between the position of the actual coherent image G (for example, the position of the center of the macula) and the designated position. Subsequently, the controller 210, so as to eliminate this displacement, that is, so as to display the coherent image G at the designated position, controls the reference mirror 174 and the scan unit 141. In this way, as shown in FIG. 14, the coherent image G is displayed at a desired position within the frame (S18).

The displacement of the coherent image G in the z direction is eliminated by adjusting the position of the reference mirror 174. Furthermore, the displacement of the coherent image G in the x direction and y direction is eliminated by adjusting the scan position of the signal light LS by the scan unit 141.

Figure 15:
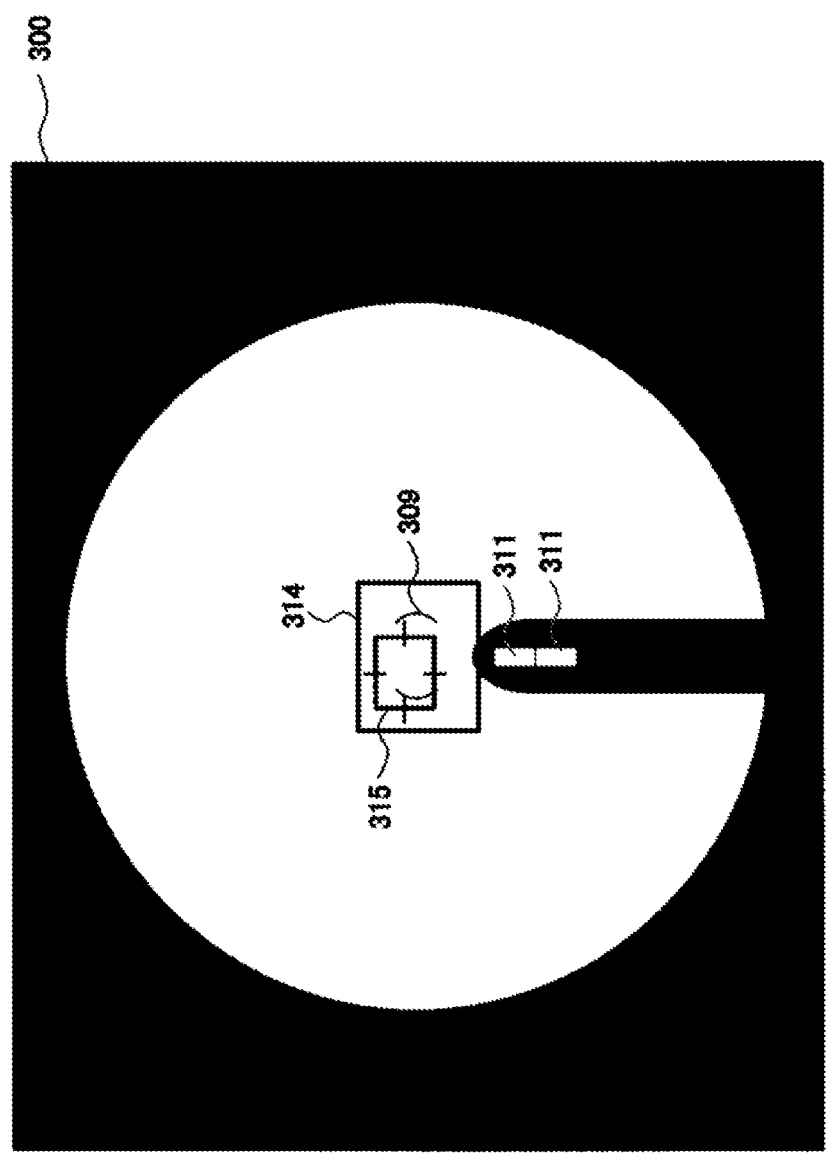
FIG. 15 is a schematic view showing an example of a configuration of a display screen in the embodiment of the optical image measuring device according to the present invention.

If the position of the coherent image G is determined to be appropriate (S16: Yes), or if the coherent image G is corrected (S18), tracking is performed of the region of interest of the fundus oculi Ef. At this time, although it is not shown in the figures, an observation image of the fundus oculi is displayed on the adjustment screen 300. The controller 210, as shown in FIG. 15, displays the scan area image 314 and the tracking area image 315, superimposing on the observation image of the fundus oculi (S19). The controller 210 then controls the scan unit 141, etc., and begins tracking (S20).

The scan area image 314 indicates the area scanned by the signal light LS, and is displayed according to the previously set aspect. The scan area image 314 shown in FIG. 15 corresponds to the abovementioned three-dimensional scan. The tracking area image 315 indicates the characteristic area of the fundus oculi Ef, which is the target of the tracking, and moves on the adjustment screen 300 in accordance with the tracking state. Tracking is performed such that the tracking area image 315 is positioned in the center of the scan area image 314.

The tracking determination part 235 determines the suitability of the tracking state (S21). This process is performed by determining whether the tracking area image 315 is contained within the scan area image 314. Moreover, it is also acceptable to determine whether the tracking area image 315 is contained in a prescribed area (vicinity of the center) within the scan area image 314.

If it is determined that the tracking state is inappropriate (S21: No), the controller 210 displays the prescribed warning information on the display 240 (S22). This warning information states, for example, the fact that tracking cannot be appropriately performed. The warning information may be character string information, or it may be image information. A message such as the following is an example of character string information: "The tracking position is outside the possible scan range." The examiner, who is aware that the tracking state is not suitable by means of the warning information, operates a manipulator 250 (for example, a fixation position adjustment key), and adjusts the fixation position of the subject's eye E such that the tracking area image 315 is contained within the scan area image 314 (S23). At this time, the tracking determination part 235 determines the suitability of the tracking state.

If the tracking state is determined to be appropriate (S21: Yes), or if the adjustment of the fixation position is completed (S23), the image processor 230 determines the respective suitability of the alignment state, the state of the focus, the position of the coherent image within the frame, and the image quality of the coherent image (S24).

If any of the conditions is determined to be inappropriate (S24: No), the same processing is performed as when the relevant condition is determined to be inappropriate (S8, S10, S15 and S17).

If all conditions are determined to be appropriate (S24: Yes), the controller 210 controls an OCT unit 150, the scan unit 141 and the image forming part 220, to form coherent images of the relevant scan area (S25). Moreover, instead of commencing this measurement automatically (auto-shoot), a message indicating that measurement is possible may be displayed. In this case, the examiner, upon seeing the message, pushes an imaging switch to commence measurement.

After obtaining the coherent image, for example, the controller 210 controls the retinal camera unit 1A and performs color imaging of the fundus oculi Ef. The obtained coherent image and the fundus oculi image are stored in the storage 212. With this, the examination is complete.

[Actions and Effects]

The actions and effects of the optical image measuring device 1 as described above will be described.

The optical image measuring device 1 has a function to obtain a tomographic image and a fundus oculi image of the fundus oculi (the measured object). The fundus oculi image is a two-dimensional image of the fundus oculi for the surface of the fundus oculi that is orthogonal to the traveling direction of the signal light LS.

Moreover, the optical image measuring device 1 has an alignment function, a focus function and a tracking function. The alignment function is implemented by an alignment part including an alignment optical system 190A. The focus function is implemented by a focusing part including a focusing optical system. The tracking part is implemented by a tracking part including the controller 210. Moreover, tracking may be performed based on a tomographic image, or it may be performed based on a fundus oculi image. A configuration for obtaining a fundus oculi image (configured as a fundus oculi camera) is one example of the "imaging part" according to the present invention.

In addition, the optical image measuring device 1 determines respectively the suitability of the alignment state, the state of the focus, the position of the tomographic image within the frame, the image quality of the tomographic image and the tracking state, and when all of these conditions are determined to be suitable, obtaining the final tomographic image is permitted. Moreover, the tomographic image used in the determination of the suitability of the conditions is provisionally obtained, and it is desirable to use a simple scan mode of the signal light LS (in the abovementioned embodiment, it is a cross-shaped scan). The distribution of the scanning points (irradiation positions of the signal light LS) does not need to be particularly dense. On the other hand, the final tomographic image is a detailed image used for diagnosis, etc., and it is desirable for the scanning point distribution to be dense (for example, a distribution at a level such that a three-dimensional image can be produced).

By means of such an optical image measuring device 1, even in the case of obtaining a tomographic image of the measured object which moves, such as a living eye, it is possible to easily perform measurement without missing the timing wherein the various conditions mentioned above are appropriate, that is, the measurement timing.

In addition, in the abovementioned embodiment, measurement is automatically performed at a timing wherein the various conditions mentioned above are suitable, and the measurement timing will not be missed.

Moreover, the optical image measuring device 1 may display warning information if any of the various conditions mentioned above is inappropriate. In this way, the examiner can be aware that the relevant condition is not suitable, and can take action to correct the relevant condition.

MODIFIED EXAMPLE

The configuration described above is merely one example for favorably implementing the present invention. Therefore, it is possible to properly make arbitrary modification within the scope of the present invention.

For example, in the abovementioned embodiment, the suitability of the alignment state, the state of the focus, the position of the tomographic image within the frame, the image quality of the tomographic image and the tracking state are respectively determined, but it is possible to omit the determination of the image quality of the tomographic image, and/or the determination of the tracking state.

In the present invention, a determination of suitability is performed for the alignment state, the state of the focus, and the position of the tomographic image within the frame. This is because these three conditions are essential for obtaining a good tomographic image. In this case, the optical image measuring device determines the suitability for each of the alignment state, the state of the focus, and the position of the tomographic image within the frame, and when all of these conditions are determined to be suitable, permits the obtaining of the final tomographic image. In addition, in the same way as the abovementioned embodiment, it is possible to have a configuration such that, when it is determined that all of the conditions are suitable, the measurements for obtaining the final tomographic image are automatically performed.

Moreover, in addition to the process of determining the abovementioned essential conditions, a configuration is possible such that a process to determine the image quality of the tomographic image or a process to determine the tracking state is performed. These ancillary conditions can be added as appropriate, taking into consideration the type (movement) of the measured object.

When any of the various conditions mentioned above is determined to be unsuitable, it is possible to have a configuration in which obtaining a tomographic image of the measured object is prohibited. As a concrete example of this, in a case wherein it is determined that a certain condition is not suitable, even if the examiner issues a command to obtain a tomographic image (by pressing the image capture switch, etc.), a configuration is possible in which the controller 210 does not accept (ignores) this command.

In the above embodiment, the position of the reference mirror 174 is changed so as to change an optical path length difference between the optical path of the signal light LS and the optical path of the reference light LR. However, a method for changing the optical path length difference is not limited thereto. For example, it is possible to change the optical path length difference by moving the retinal camera unit 1A and the OCT unit 150 with respect to the eye E to change the optical path length of the signal light LS. To be specific, for example, in a case that a measured object is not a living site, it is also effective to change the optical path length difference by moving the measured object in the depth direction.

The computer program used in the above embodiment can be stored in any kind of recording medium that can be read by a drive device of a computer. As this recording medium, for example, an optical disk, a magneto-optic disk (CD-ROM, DVD-RAM, DVD-ROM, MO, and so on), and a magnetic storing medium (a hard disk, a floppy disk (TM), ZIP, and so on) can be used. Moreover, it is possible to store into a storing device such as a hard disk drive and a memory. Besides, it is possible to transmit/receive this program through a network such as the the internet and a LAN.

The invention claimed is:

1. An optical image measuring device comprising:
   an optical system that splits a light beam from a light source into signal light and reference light, generates interference light by causing said signal light propagated through a fundus oculi of an eye to be examined and said reference light propagated through a reference object to interfere, and generates detection signals by detecting said interference light; and
   an image forming circuit that forms a tomographic image of said fundus oculi based on said detection signals;
   said optical image measuring device comprising a first processor, the optical image measuring device further comprising:
   an alignment part that projects an alignment bright point from a second light source to the eye in order to perform alignment of said optical system with respect to the fundus oculi;
   a focusing part that focuses said optical system with respect to a region of interest of said fundus oculi;
   a determining part, comprised by said first processor, that determines the suitability of the position of said optical system after the alignment by said alignment part, the suitability of the focus state after the focusing by said focusing part, and the suitability of the position of the tomographic image of said region of interest in a frame after the tomographic image is formed by said image forming circuit; and
   a controller, comprising a second processor or comprised by said first processor, that, when it is determined that all of the position of said optical system, the position of said focus state and the position in said frame are appropriate through repeated suitability determination, controls said optical system and said image forming circuit, making it possible to obtain the tomographic image of said region of interest, wherein
   the determinations of a series of the suitability of the position of said optical system, the suitability of the focus state, and the suitability of the position of the tomographic image of said region of interest are repeated after the determinations are all completed once.

2. The optical image measuring device according to claim 1, wherein:
   said controller, when it is determined that at least one of the position of said optical system, the position of said focus state and the position in said frame is not appropriate, prohibits the acquisition of the tomographic image of said measured object.

3. The optical image measuring device according to claim 1 further comprising:
   a display,
   wherein said controller, when it is determined that at least one of the position of said optical system, the position of said focus state and the position in said frame is not appropriate, causes said display to display warning information.

4. The optical image measuring device according to claim 1, wherein:
   said determining part further analyzes the tomographic image that is formed by said image forming circuit and determines the suitability of the image quality of said tomographic image, and
   said controller, when it is determined that all the position of said optical system, the position of said focus state and the position in said frame are appropriate, controls said optical system and said image forming circuit, making it possible to obtain the tomographic image of said region of interest.

5. The optical image measuring device according to claim 4, wherein:
   said controller, when it is determined that at least one of the position of said optical system, the position of said focus state, the position in said frame and the image quality of said tomographic image is not appropriate, prohibits acquisition of the tomographic image of said measured object.

6. The optical image measuring device according to claim 4 further comprising:
a display,
wherein said controller, when it is determined that at least one of the position of said optical system, the position of said focus state, the position in said frame and the image quality of said tomographic image is not appropriate, causes said display to display warning information.

7. The optical image measuring device according to claim 4, wherein:
said optical system comprises a polarizing plate on an optical path of said reference light,
wherein said controller, when it is determined that the image quality of said tomographic image is not appropriate, controls said polarizing plate such that the image quality becomes its maximum.

8. The optical image measuring device according to claim 1 further comprising:
a tracking part comprised by the controller that, based on the tomographic image that is formed by said image forming circuit, causes the irradiation position of said signal light with respect to said measured object to track movement of said measured object such that the tomographic image of said region of interest is disposed in substantially the middle inside of said frame,
wherein
said determining part further determines the suitability of the tracking state of the irradiation position of said signal light, and
said controller, when it is determined that all of the position of said optical system, the position of said focus state, the position in said frame, and said tracking state are appropriate, controls said optical system and said image forming circuit, making it possible to obtain the tomographic image of said region of interest.

9. The optical image measuring device according to claim 1 further comprising:
an imaging part that images a 2-dimensional image of said measured object on the surface that is substantially perpendicular to the traveling direction of said signal light with respect to said measured object; and
a tracking part, comprised by the controller, that, based on said 2-dimensional image that is imaged, causes the irradiation position of said signal light with respect to said measured object to track movement of said measured object such that the tomographic image of said region of interest is disposed in substantially the middle inside of said frame,
wherein
said determining part further determines the suitability of the tracking state of the irradiation position of said signal light, and
said controller, when it is determined that all of the position of said optical system, the position of said focus state, the position in said frame, and said tracking state are appropriate, controls said optical system and said image forming circuit, making it possible to obtain the tomographic image of said region of interest.

10. The optical image measuring device according to either claim 8 or claim 9, wherein:
said controller, when it is determined that at least one of the position of said optical system, the position of said focus state, the position in said frame and said tracking state is not appropriate, prohibits acquisition of the tomographic image of said measured object.

11. The optical image measuring device according to either claim 8 or claim 9, further comprising:
a display,
wherein said controller, when it is determined that at least one of the position of said optical system, the position of said focus state, the position inside said frame and said tracking state is not appropriate, causes said display to display warning information.

12. An optical image measuring device comprising:
an optical system that splits a light beam from a light source into signal light and reference light, generates interference light by causing said signal light propagated through a fundus oculi of an eye to be examined and said reference light propagated through a reference object to interfere, and generates detection signals by detecting said interference light; and
an image forming circuit that forms a tomographic image of said fundus oculi based on said detection signals;
said optical image measuring device comprising a first processor, the optical image measuring device further comprising:
an alignment part that projects an alignment bright point from a second light source to the eye in order to perform alignment of said optical system with respect to the fundus oculi;
a focusing part that focuses said optical system with respect to a region of interest of said fundus oculi;
a tracking part, comprised by a second processor, that, based on the tomographic image that is formed by said image forming circuit, causes the irradiation position of said signal light with respect to said fundus oculi to track movement of said fundus oculi such that the tomographic image of said region of interest is disposed in substantially the middle inside of said frame,
a determining part, comprised by said first processor or comprised by a second processor, that determines the suitability of the position of said optical system after the alignment by said alignment part, determines the suitability of the focus state after the focusing by said focusing part, determines the suitability of the position of the tomographic image of said region of interest in a frame after the tomographic image is formed by said image forming circuit, determines the suitability of the image quality of said tomographic image by analyzing the tomographic image that is formed by said image forming circuit, and determines the suitability of the tracking state of the irradiation position of said signal light; and
a controller, comprised by said second processor, that, when it is determined that all of the position of said optical system, the position of said focus state, the position inside said frame, and said tracking state are appropriate through repeated suitability determination, controls said optical system and said image forming circuit, making it possible to obtain the tomographic image of said region of interest.

13. An optical image measuring device comprising:
an optical system that splits a light beam from a light source into signal light and reference light, generates interference light by causing said signal light propagated through a fundus oculi of an eye to be examined and said reference light propagated through a reference object to interfere, and generates detection signals by detecting said interference light;

an image forming circuit that forms part for forming a tomographic image of fundus oculi, based on said detection signals; and an imaging part that images a 2-dimensional image of said fundus oculi on the surface that is substantially perpendicular to the traveling direction of said signal light, with respect to said fundus oculi; and said optical image measuring device comprising a first processor, the optical image measuring device further comprising:

an alignment part that projects an alignment bright point from a second light source to the eye in order to perform alignment of said optical system with respect to the fundus oculi;

a focusing part that focuses said optical system with respect to the region of interest of said fundus oculi;

a tracking part, comprised by said first processor, that, based on said 2-dimensional image that is imaged, causes the irradiation position of said signal light with respect to said fundus oculi to track movement of said fundus oculi such that the tomographic image of said region of interest is disposed in substantially the middle inside of said frame;

a determining part, comprised by said first processor or comprised by a second processor, that determines the suitability of the position of said optical system after the alignment by said alignment part, determines the suitability of the focus state after the focusing by said focusing part, determines the suitability of the position of the tomographic image of said region of interest in a frame after the tomographic image is formed by said image forming circuit, determines the suitability of the image quality of said tomographic image by analyzing the tomographic image that is formed by said image forming circuit, and determines the suitability of the tracking state of the irradiation position of said signal light; and a controller, comprised by said first processor, that, when it is determined that all of the position of said optical system, the position of said focus state, the position inside said frame, and said tracking state are appropriate through repeated suitability determination, controls said optical system and said image forming circuit, making it possible to obtain the tomographic image of said region of interest.

14. The optical image measuring device according to either claim 1, claim 4, claim 8, claim 9, claim 12, or claim 13, wherein:

said controller, when it is determined that all of the conditions are appropriate, controls said optical system and said image forming circuit, causing them to obtain the tomographic image of said region of interest.

* * * * *

UNITED STATES PATENT AND TRADEMARK OFFICE
CERTIFICATE OF CORRECTION

| | |
|---|---|
| PATENT NO. | : 8,970,847 B2 |
| APPLICATION NO. | : 13/147536 |
| DATED | : March 3, 2015 |
| INVENTOR(S) | : Yusuke Ono |

It is certified that error appears in the above-identified patent and that said Letters Patent is hereby corrected as shown below:

In the specification,

Column 5, line 1, "t he" should read -- the --.

Column 5, line 20, "t he" should read -- the --.

Column 5, line 28, "t he" should read -- the --.

Signed and Sealed this
Twenty-first Day of July, 2015

Michelle K. Lee
*Director of the United States Patent and Trademark Office*